US009538927B2

(12) United States Patent
Thaveeprungsriporn et al.

(10) Patent No.: US 9,538,927 B2
(45) Date of Patent: Jan. 10, 2017

(54) OPTICAL MEASUREMENT DEVICE AND A METHOD FOR AN OPTICAL MEASUREMENT

(75) Inventors: Visit Thaveeprungsriporn, Synapse (SG); Md. Irwan bin Md. Kassim, Synapse (SG)

(73) Assignee: Nitto Denko Corporation, Osaka (JP)

(*) Notice: Subject to any disclaimer, the term of this patent is extended or adjusted under 35 U.S.C. 154(b) by 180 days.

(21) Appl. No.: 13/884,509

(22) PCT Filed: Jan. 5, 2012

(86) PCT No.: PCT/SG2012/000005
§ 371 (c)(1),
(2), (4) Date: Jul. 25, 2013

(87) PCT Pub. No.: WO2012/099537
PCT Pub. Date: Jul. 26, 2012

(65) Prior Publication Data
US 2013/0296673 A1 Nov. 7, 2013

Related U.S. Application Data

(63) Continuation-in-part of application No. 13/010,705, filed on Jan. 20, 2011, now Pat. No. 8,761,853.

(51) Int. Cl.
*A61B 5/1455* (2006.01)
*A61B 5/0295* (2006.01)
(Continued)

(52) U.S. Cl.
CPC ........... *A61B 5/0295* (2013.01); *A61B 5/0059* (2013.01); *A61B 5/02416* (2013.01);
(Continued)

(58) Field of Classification Search
CPC . A61B 5/1455; A61B 5/14551; A61B 5/0295; A61B 5/02416; A61B 5/6898; A61B 5/0059; A61B 5/7435; A61B 2562/0247
See application file for complete search history.

(56) References Cited

U.S. PATENT DOCUMENTS

| 5,954,644 A | 9/1999 | Dettling et al. |
| 6,360,113 B1 | 3/2002 | Dettling |

(Continued)

FOREIGN PATENT DOCUMENTS

| CN | 1885863 A | 12/2006 |
| CN | 101411613 A | 4/2009 |

(Continued)

OTHER PUBLICATIONS

Office Action issued in counterpart Chinese Application No. 201280003880.7 mailed on Jul. 25, 2014 (26 pages).

(Continued)

*Primary Examiner* — Eric Winakur
(74) *Attorney, Agent, or Firm* — Osha Liang LLP

(57) ABSTRACT

A reflectance-based optical measurement device and a method for a reflectance-based optical measurement are provided. The device comprises an illumination and detection assembly configured to output light to a surface portion of a user for measurement and to detect the output light reflected from said surface portion of the user as a signal; a coupling member configured for coupling in a cableless configuration to a personal mobile processing device; a measurement surface configured to allow access to said measurement surface by the surface portion of the user; wherein said access is provided by the optical device being holderless such that the surface portion of the user is allowed access to said measurement surface from all directions in a single plane; and further wherein said coupling member is arranged to transmit the detected signal to the personal mobile processing device.

18 Claims, 36 Drawing Sheets

(51) Int. Cl.
  *G01N 21/31* (2006.01)
  *A61B 5/024* (2006.01)
  *A61B 5/00* (2006.01)

(52) U.S. Cl.
  CPC ........ *A61B 5/1455* (2013.01); *A61B 5/14551* (2013.01); *A61B 5/6843* (2013.01); *A61B 5/6898* (2013.01); *G01N 21/3151* (2013.01); *A61B 5/7203* (2013.01); *A61B 5/7435* (2013.01); *A61B 2562/0247* (2013.01); *A61B 2562/227* (2013.01); *F04C 2270/041* (2013.01); *G01N 2021/3144* (2013.01)

(56) References Cited

U.S. PATENT DOCUMENTS

| | | | |
|---|---|---|---|
| 2005/0187448 A1 | 8/2005 | Petersen et al. | |
| 2005/0228244 A1 | 10/2005 | Banet | |
| 2010/0056880 A1* | 3/2010 | Cho et al. | 600/323 |
| 2010/0222655 A1 | 9/2010 | Starr et al. | |
| 2010/0305418 A1 | 12/2010 | Deliwala | |

FOREIGN PATENT DOCUMENTS

| | | |
|---|---|---|
| CN | 101827555 A | 9/2010 |
| WO | 2009052704 A1 | 4/2009 |

OTHER PUBLICATIONS

International Search Report issued in PCT/SG2012/000005 mailed Mar. 23, 2012 (2 pages).
International Preliminary Report on Patentability issued in PCT/SG2012/000005 mailed Dec. 4, 2012 (12 pages).
Office Action issued in counterpart Chinese Patent Application No. 201280003880.7 mailed on Mar. 9, 2015 (15 pages).
Extended European Search Report in corresponding European Application No. 12736805.8 dated Sep. 11, 2015 (8 pages).
http://www.nasa.gov/centers/ames/news/features/2009/cell_phone_sensors.html "NASA Ames Scientist Develops Cell Phone Chemical Sensor" Oct. 30, 2009 (2 pages).
Office Action in corresponding Chinese Application No. 201280003880.7 dated Dec. 18, 2015 (11 pages).
Office Action issued in counterpart Chinese Patent Application No. 201280003880.7 mailed on Jul. 29, 2015 (23 pages).

* cited by examiner

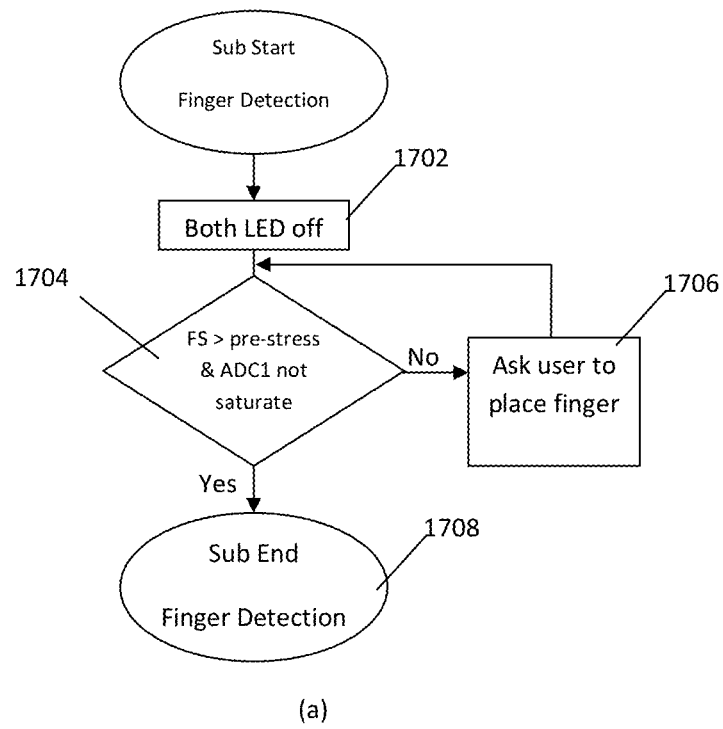
(a)
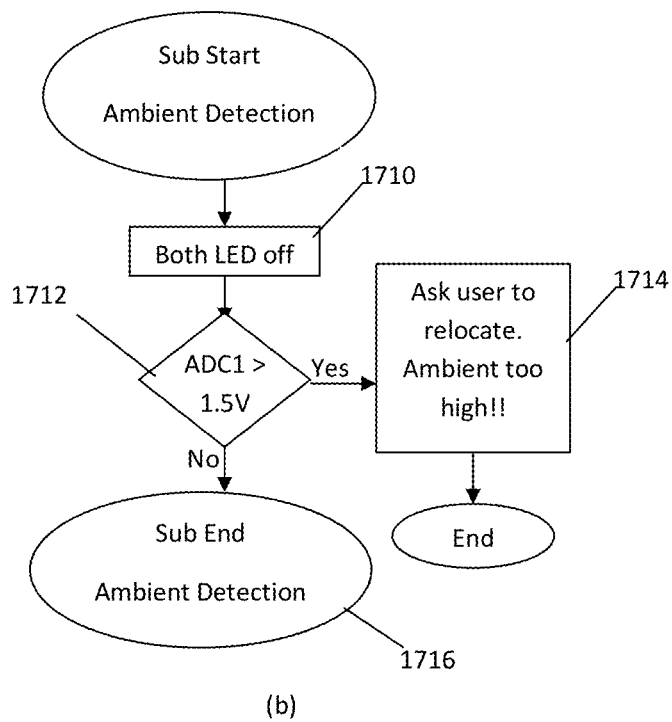
(b)
Figure 17

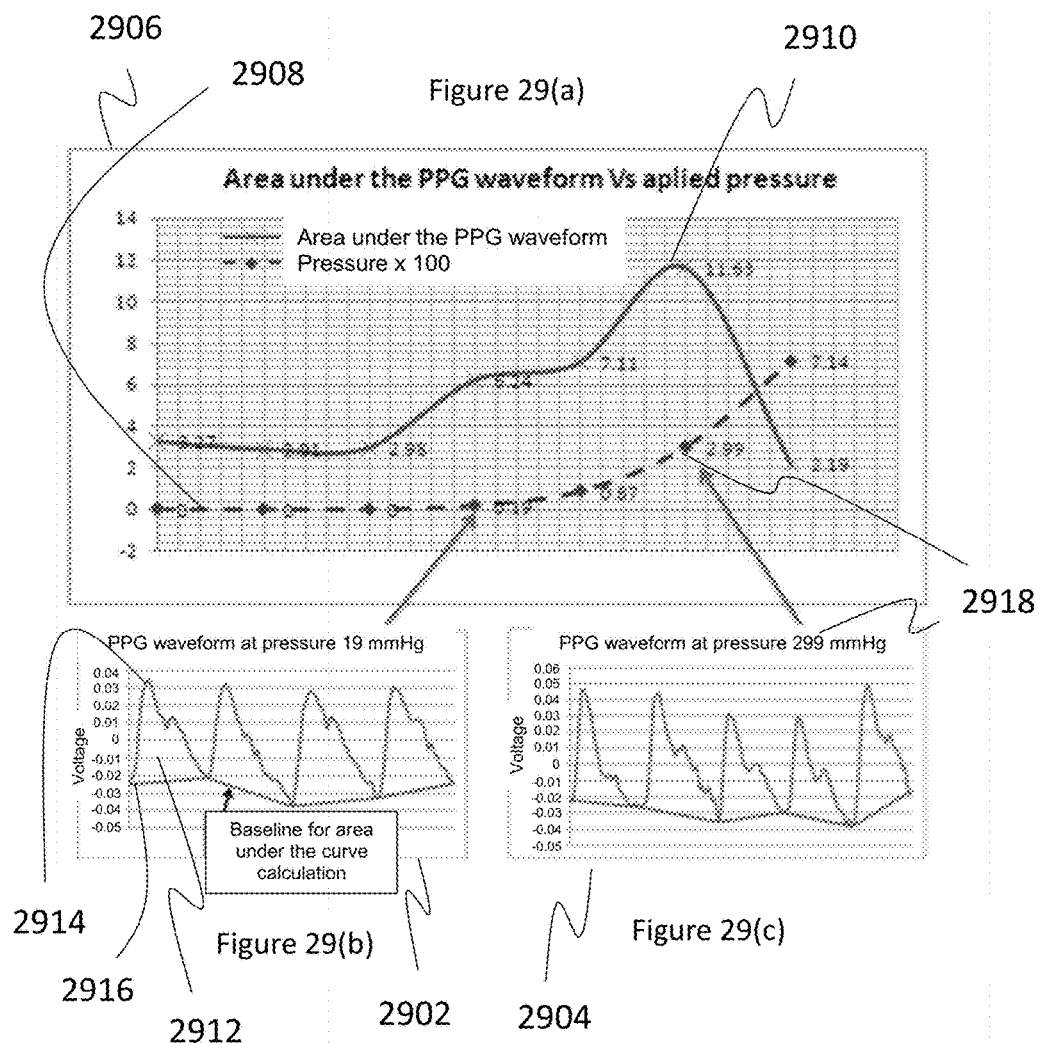

OPTICAL MEASUREMENT DEVICE AND A METHOD FOR AN OPTICAL MEASUREMENT

CROSS-REFERENCE TO RELATED APPLICATIONS

This application is a national phase application of PCT/SG2012/000005 (hereinafter "international application"), filed on Jan. 5, 2012. The international application is a continuation-in-part (CIP) of U.S. patent application Ser. No. 13/010,705 (hereinafter "priority application"), filed on Jan. 20, 2011. The priority application is hereby incorporated by reference in its entirety.

TECHNICAL FIELD

The present invention relates broadly to a reflectance-based optical measurement device and to a method for a reflectance-based optical measurement.

BACKGROUND

Optical monitoring of physiological characteristics utilizes the detection of light transmitted through a location of a user being measured. Photoplethysmography (PPG) is an optical measurement technique used to detect blood volume changes in the microvascular bed of living tissue, typically by detecting light transmitted through the ear lobe or fingertip. As arterial pulsations enter the capillary bed, changes in the volume of the blood vessels or characteristics of the blood itself modify the optical properties of the capillary bed. A PPG signal is used to measure saturation of peripheral oxygen (SpO2), which is an estimation of the level of oxygen saturation in a fluid, such as blood. The PPG signal can also be used to measure blood pressure.

A device such as a pulse oximeter provides for measuring enhanced optical pulsatile signals emitted by the changes in the volume of blood flowing through a user. The pulse oximeter typically has a pair of small light emitting diodes (LEDs) facing a photodiode/photodetector, with a translucent part of the user's body, usually a fingertip or an earlobe, positioned there between. The LEDs illuminate the tissue (e.g. skin) of the user and the photodetector measures small variations in light intensity associated with changes in perfusion in a catchment volume. An oximeter in such a configuration is typically called a transmittance-type oximeter. The light from the LEDs passes through the tissue and is detected by the photodiode. One LED is red, with wavelength of approximately 660 nanometers (nm), and the other is infrared, with a wavelength of approximately 905, 910 or 940 nm. Absorption at these wavelengths differs significantly between oxyhemoglobin and its deoxygenated form. Therefore, the ratio of oxyhemoglobin to deoxyhemoglobin can be calculated from the ratio of the absorption of the red and infrared light, i.e. the ratio of red light to infrared light absorption of pulsating components at the measuring site.

For transmittance-type oximeters, a cuff or holder is typically provided to function primarily as a holder for the photodiode and also as a shield against ambient light. It has been recognised that having a cuff or a holder/clip typically enforces a fixed orientation of the part of the user's body for measurement. This may be undesirable to a user.

On the other hand, apart from transmittance-type oximeters, there also exist reflectance-type oximeters. For reflectance-type oximeters, the LEDs and the photodiode reside on the same side of the translucent part of the user's body. Light from the LEDs are reflected from the portion to be measured and detected by the photodiode. For reflectance-type oximeters, ambient light can be a significant factor in accuracy of light detection by the photodiode. Thus, reflectance-type oximeters typically still require a cuff or a holder/clip to provide shielding against ambient light from interfering with reflected light from the LEDs. This may be undesirable to a user.

Furthermore, for certain types of reflectance-type oximeters without clips, such as those in patch form, a shield is still required on the base of the oximeter to provide the ambient light shielding.

Further to the above, the inventors have recognised that a typical oximeter has relatively complicated design considerations centering on how to incorporate a power source such that the oximeter can function as a standalone device. This may delay development and increase production costs for oximeters.

In addition, for oximeters, ambient light can interfere with readings in the form of ambient noise. For example, ambient light such as those from bilirubin lamps, fluorescent light, infrared heating lamps and direct sunlight etc. can affect the accuracy of SpO2 readings. As a brief introduction, SpO2 calculation is based on the AC and DC components of both a red (RED) and an infra-red (IR) PPG signal. The Red PPG signal is obtained when a red LED of e.g. about 660 nm is reflected off the skin of a user. The IR PPG signal is obtained when an IR LED emitting electromagnetic waves of e.g. about 940 nm is reflected off the skin of a user.

Therefore, without removing ambient light interference from the PPG signals, a true reading of Red or IR PPG signals cannot be acquired. This in turn affects the calculation of SpO2. Typically, a third PPG signal, i.e. ambient PPG, is obtained. This ambient PPG signal is a signal obtained by a photodetector when both the IR and Red LEDs are turned off. Typically, an on-the-fly point-by-point subtraction of the ambient signal from the Red and IR PPG signals is carried out. However, it has been recognised by the inventors that such processing is typically power consuming. Digital reconstruction of PPG signals can also be time consuming. It has also been recognised by the inventors that the above processing may further typically require additional and relatively complicated multi-path circuitry, e.g. a different signal path for Red, Infrared and/or ambient PPG signals.

Thus, in view of the above, there exists a need for an optical measurement device and method that seek to address at least one of the above problems. There also exists a need for a noise cancellation method and system that seek to address at least one of the above problems.

SUMMARY

In accordance with an aspect of the present invention, there is provided a reflectance-based optical measurement device comprising an illumination and detection assembly configured to output light to a surface portion of a user for measurement and to detect the output light reflected from said surface portion of the user as a signal; a coupling member configured for coupling in a cableless configuration to a personal mobile processing device; a measurement surface configured to allow access to said measurement surface by the surface portion of the user; wherein said access is provided by the optical device being holderless such that the surface portion of the user is allowed access to said measurement surface from all directions in a single plane; and further wherein said coupling member is arranged to transmit the detected signal to the personal mobile processing device.

The single plane may be on a same plane as said measurement surface.

The device being holderless may allow an unshielded configuration whereby ambient light noise is transmitted with said detected signal.

The device may further comprise a pressure assembly configured to detect an amount of pressure applied to the illumination and detection assembly by said surface portion of the user.

The device may further comprise a housing structure for housing the illumination and detection assembly and wherein the housing structure provides structural rigidity to the device.

The cableless configuration may comprise a coupling means of the coupling member in a form of a universal serial bus (USB) port or a 30-pin port.

The signal may be a photoplethysmography (PPG) signal.

The illumination and detection assembly may comprise a red light emitting diode (LED), an infra-red LED or both.

Saturation of peripheral oxygen (SpO2) information of the user may be derivable from the detected signal from both the red LED and the infra-red LED.

The measurement device may function as an accessory to the personal mobile processing device.

The personal mobile processing device may be one selected from a group consisting of a mobile phone, a smartphone, a personal digital assistant (PDA), a mobile music player, a tablet computer, a netbook and a laptop.

In accordance with another aspect of the present invention, there is provided a method for a reflectance-based optical measurement, the method comprising allowing access to a measurement surface by a surface portion of a user for measurement wherein the surface portion of the user is allowed access to said measurement surface from all directions in a single plane; outputting light to said surface portion of the user for measurement, detecting the output light reflected from said surface portion of the user as a signal; coupling to a personal mobile processing device in a cableless configuration; and transmitting the detected signal to the personal mobile processing device.

The step of detecting the output light may be performed in an unshielded configuration whereby ambient light noise is transmitted in the transmitting step with said detected signal.

The method may further comprise detecting an amount of pressure applied by said surface portion of the user.

The step of outputting light may comprise using a red light emitting diode (LED), an infra-red LED or both.

The method may further comprise deriving saturation of peripheral oxygen (SPO2) information of the user from the detected signal from both the red LED and the infra-red LED.

In accordance with another aspect of the present invention, there is provided a computer readable data storage medium having stored thereon computer code means for instructing a processor to execute a method for a reflectance-based optical measurement, the method comprising allowing access to a measurement surface by a surface portion of a user for measurement wherein the surface portion of the user is allowed access to said measurement surface from all directions in a single plane; outputting light to said surface portion of the user for measurement, detecting the output light reflected from said surface portion of the user as a signal; coupling to a personal mobile processing device in a cableless configuration; and transmitting the detected signal to the personal mobile processing device.

The computer readable data storage medium, wherein the method may comprise performing the step of detecting the output light in an unshielded configuration whereby ambient light noise is transmitted in the transmitting step with said detected signal.

The computer readable data storage medium, wherein the method may comprise using a red light emitting diode (LED), an infra-red LED or both, in the step of outputting light.

The computer readable data storage medium, wherein the method may further comprise deriving saturation of peripheral oxygen (SPO2) information of the user from the detected signal from both the red LED and the infra-red LED.

BRIEF DESCRIPTION OF THE DRAWINGS

Example embodiments of the invention will be better understood and readily apparent to one of ordinary skill in the art from the following written description, by way of example only, and in conjunction with the drawings, in which:

FIG. 17(a) is a schematic flow diagram illustrating a finger detection process in an example embodiment.

FIG. 17(b) is a schematic flow diagram illustrating an ambient light detection process in an example embodiment.

FIGS. 29(a) to (c) are schematic graphical representations showing a correlation between a PPG waveform and an applied pressure in an example embodiment.

DETAILED DESCRIPTION

Figure 1:
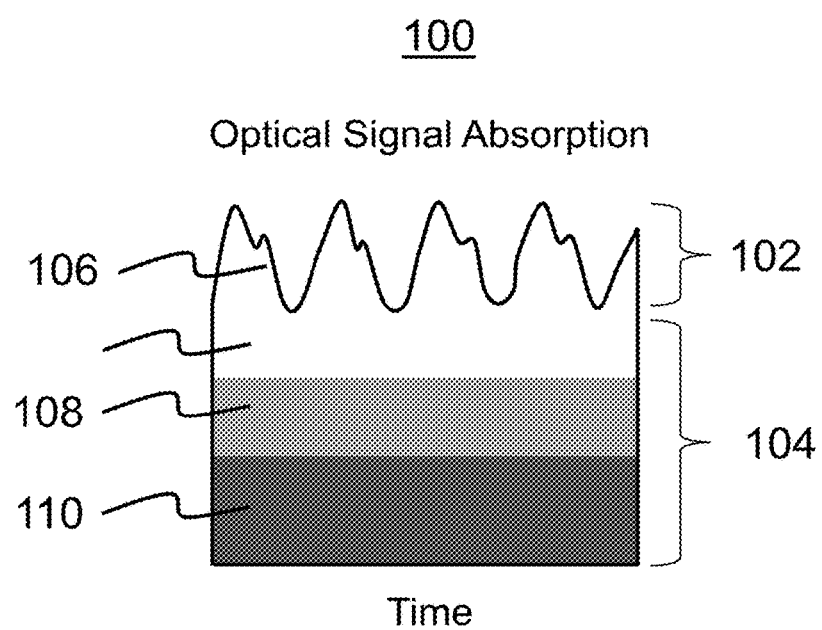
FIG. 1 illustrates a graphical representation of a photoplethysmograph (PPG) signal.

The example embodiments described herein can provide an optical measurement device and method that can obtain a photoplethysmography (PPG) signal from a user. The measurements in the example embodiments are non-invasive optical physiological measurements.

In an example implementation, a reflectance-based optical measurement device can be provided that functions as an accessory to a personal mobile processing device. The personal mobile processing device can be a mobile phone, smartphone, personal digital assistant (PDA), mobile music player, tablet, netbook or laptop, although this list is not exhaustive by any means. In such a function, the accessory is not meant to affect the main workings or functions of the personal mobile processing device. In example implementations, the optical measurement device is preferably smaller than a palm-sized object for portability.

The measurement device comprises a coupling member that can provide coupling between the measurement device to the personal mobile processing device in a cableless configuration. In the description, cableless is taken to include a connection that is without the use of wires or cables extending from the personal mobile processing device to the optical measurement device.

In the example implementation, the measurement device is provided without a holder or clip or cuff, i.e. the measurement device is holderless, for engaging a surface portion, such as a finger tip of a user, for measurement. A measurement surface is provided for the measurement device such that the user can access the measurement surface using the surface portion for measurement. With the measurement device being holderless, the surface portion of the user can access the measurement surface from all directions in a single plane. The single plane may be on a same plane as the measurement surface.

In the example implementation, the measurement device is used for illuminating a surface portion of the user and detecting reflected light from the surface portion. The measurement device, being meant as an accessory, transmits the detected light information to another device, for e.g. the personal mobile processing device, to carry out further processing, e.g. for removal of ambient light interference for SpO2 values determination. It will be appreciated that some extent of ambient light interference can be allowed in the light detection at the measurement device given that the measurement device does not provide shielding for light reflection. Thus, in the example implementation, the measurement device is not processor-intensive, e.g. may not require a processor, and can therefore function without a dedicated power supply such as a battery. Thus, the measurement device can be manufactured to be relatively small as compared to conventional devices.

In the example implementation, the measurement device is in a substantially non-deformable form, as opposed to patch-type oximeters. The measurement surface of the measurement device is also preferably non-adhesive to reduce the likelihood of inconvenience to users.

Before proceeding to more fully describe some example embodiments, it may be beneficial to briefly describe components of a PPG signal.

Figure 2:
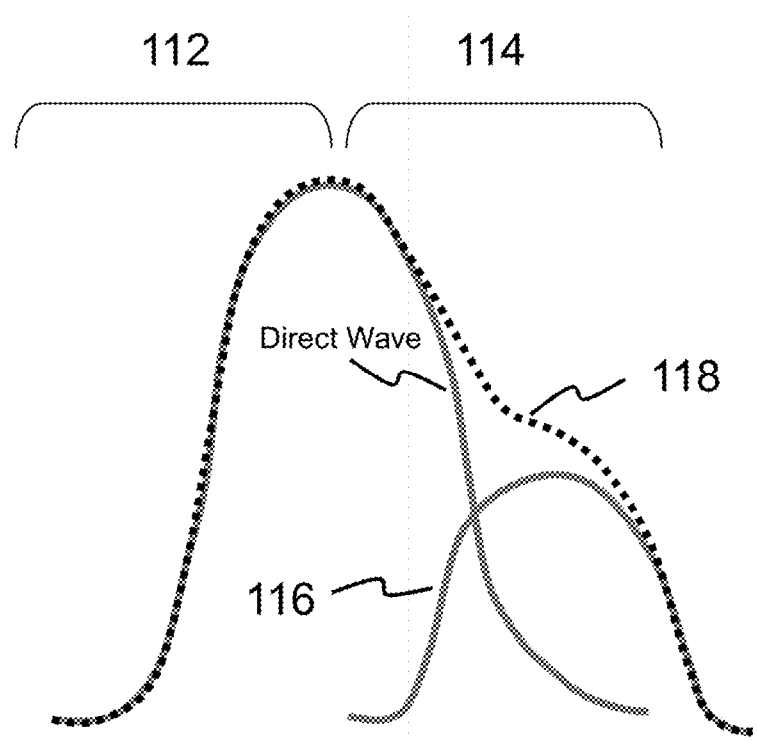
FIG. 2 is an illustration of an alternating current (AC) pulse waveform of a PPG signal.

FIGS. 1 and 2 are provided to briefly describe components of a PPG signal. FIG. 1 illustrates a graphical representation of a photoplethysmograph (PPG) signal 100, which can generally be divided into two components: an AC component 102 due to the absorption of light in pulsatile arterial blood volume 106; and a DC component 104 caused by the absorption produced by non-pulsatile arterial blood—i.e. venous blood and capillary blood 108, and tissue absorption 110.

In FIG. 1, this AC component 102 is superimposed onto a large quasi-DC component 104 that relates to the tissues and to the average blood volume. This DC component 104 varies slowly due to respiration, vasomotor activity and vasoconstrictor waves. With suitable electronic filtering and amplification, both the AC component 102 and DC component 104 can be extracted for subsequent pulse wave analysis.

Two significant characteristics of the PPG AC pulse waveform 102 have been described and are illustrated in FIG. 2, where the appearance of the pulse waveform was defined as two phases: a first anacrotic phase 112 being the rising edge of the pulse, and a second catacrotic phase 114 being the falling edge of the pulse. The first phase 112 is primarily concerned with systole, while the second phase 114 represents diastole and wave reflections 116 from the periphery. A dicrotic notch 118 is usually seen in the second catacrotic phase 114 of subjects with healthy compliant arteries.

In the following detailed description, reference will be made to the accompanying drawings. The aforementioned accompanying drawings show by way of illustration and not by way of limitation, specific embodiments and implementations consistent with principles of the present invention. These implementations are described in sufficient detail to enable those skilled in the art to practice the invention, and it is to be understood that other implementations may be utilized and that structural changes and/or substitutions of various elements may be made without departing from the scope of the present invention. The following detailed description is, therefore, not to be construed in a limited sense. Additionally, the various embodiments as described may be implemented in the form of software running on a general purpose computer, in the form of a specialized hardware, or combination of software and hardware.

The terms "coupled" or "connected" as used in this description are intended to cover both directly connected or connected through one or more intermediate means, unless otherwise stated.

The description herein may be, in certain portions, explicitly or implicitly described as algorithms and/or functional operations that operate on data within a computer memory or an electronic circuit. These algorithmic descriptions and/or functional operations are usually used by those skilled in the information/data processing arts for efficient description. An algorithm is generally relating to a self-consistent sequence of steps leading to a desired result. The algorithmic steps can include physical manipulations of physical quantities, such as electrical, magnetic or optical signals capable of being stored, transmitted, transferred, combined, compared, and otherwise manipulated.

Further, unless specifically stated otherwise, and would ordinarily be apparent from the following, a person skilled in the art will appreciate that throughout the present specification, discussions utilizing terms such as "scanning", "calculating", "determining", "replacing", "generating", "initializing", "outputting", and the like, refer to action and processes of a instructing processor/computer system, or similar electronic circuit/device/component, that manipulates/processes and transforms data represented as physical quantities within the described system into other data similarly represented as physical quantities within the system or other information storage, transmission or display devices etc.

The description also discloses relevant device/apparatus for performing the steps of the described methods. Such apparatus may be specifically constructed for the purposes of the methods, or may comprise a general purpose computer/processor or other device selectively activated or reconfigured by a computer program stored in a storage member. The algorithms and displays described herein are not inherently related to any particular computer or other apparatus. It is understood that general purpose devices/machines may be used in accordance with the teachings herein. Alternatively, the construction of a specialized device/apparatus to perform the method steps may be desired.

In addition, it is submitted that the description also implicitly covers a computer program, in that it would be clear that the steps of the methods described herein may be put into effect by computer code. It will be appreciated that a large variety of programming languages and coding can be used to implement the teachings of the description herein. Moreover, the computer program if applicable is not limited to any particular control flow and can use different control flows without departing from the scope of the invention.

Furthermore, one or more of the steps of the computer program if applicable may be performed in parallel and/or sequentially. Such a computer program if applicable may be stored on any computer readable medium. The computer readable medium may include storage devices such as magnetic or optical disks, memory chips, or other storage devices suitable for interfacing with a suitable reader/general purpose computer. The computer readable medium may even include a wired medium such as exemplified in the Internet system, or wireless medium such as exemplified in bluetooth technology. The computer program when loaded and executed on a suitable reader effectively results in an apparatus that can implement the steps of the described methods.

The example embodiments may also be implemented as hardware modules. A module is a functional hardware unit designed for use with other components or modules. For example, a module may be implemented using digital or discrete electronic components, or it can form a portion of an entire electronic circuit such as an Application Specific Integrated Circuit (ASIC). A person skilled in the art will understand that the example embodiments can also be implemented as a combination of hardware and software modules.

In some example embodiments, saturation of peripheral oxygen (SPO2) information of a user is derivable from detected output light information from both a red LED and an infra-red LED. Further, in the description herein, the term "light" as used herein is meant to be interpreted in a broad sense and is not limited to visible light only. The term "light"

as used herein can include, but is not limited to, X-ray light rays, visible light rays, ultraviolet light rays and infra-red light rays.

Figure 3:
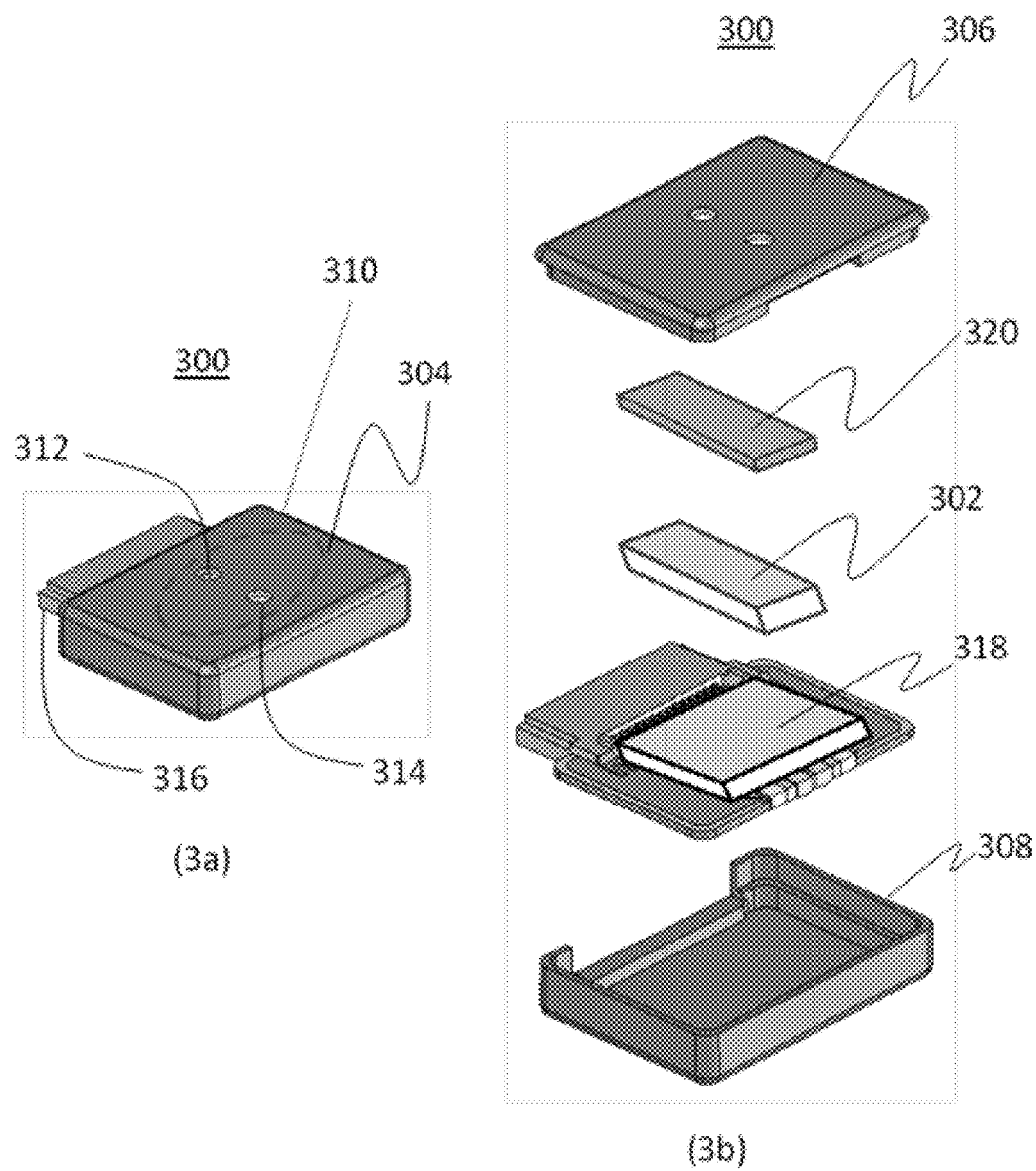
FIG. 3(a) is a schematic illustration of an optical measurement device in an example embodiment.
FIG. 3(b) shows schematically an exploded view of the optical measurement device.
FIG. 3(c) is a diagram illustrating optical transmission characteristics of optical filtering in an example embodiment.
Figure 3:
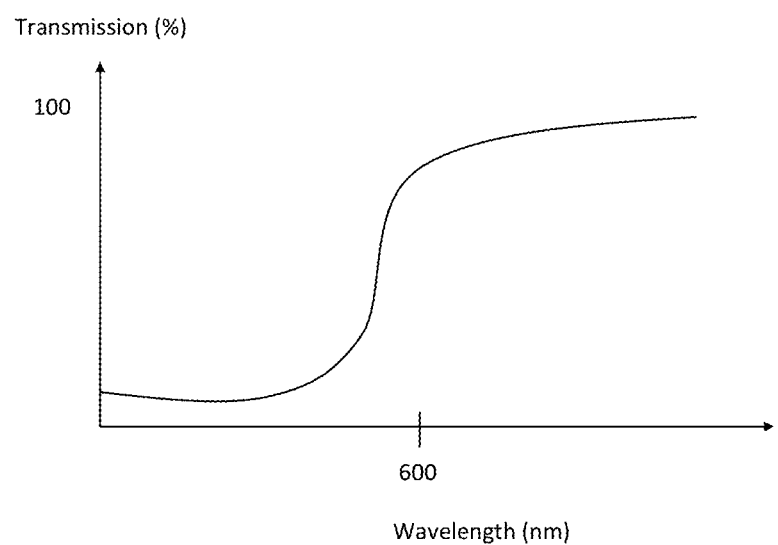

FIG. 3(a) is a schematic illustration of an optical measurement device in an example embodiment. FIG. 3(b) shows schematically an exploded view of the optical measurement device.

The optical measurement device 300 is a reflectance-based device in the example embodiment. The optical measurement device 300 comprises an illumination and detection assembly 302 encased in a housing 304. In the exploded view in FIG. 3(b), the housing 304 is shown divided into a top casing 306 and a base casing 308. The top casing 306 comprises a measurement surface 310, shown schematically with dotted lines. The measurement site/surface 310 is coupled to a light source 312 and one or more light detectors e.g. 314 of the illumination and detection assembly 302. The optical measurement device 300 further comprises a coupling member 316 that can provide coupling between the measurement device 300 to a personal mobile processing device/feedback unit (not shown) in a cableless configuration. The coupling member 316 may be in the form of an interface port such as a universal serial bus (USB) port or the 30 pin connection used in the Apple® iPhone® (Apple Computer, Inc., Cupertino, Calif.) etc.

In the example embodiment, the light source 312 can propagate light through a surface portion of a user for measurement, e.g. a portion of living tissue of the user placed at the measurement site. The light detectors e.g. 314 can detect light reflected from the portion of living tissue of the user. The detected light information at the light detectors e.g. 314 can be transmitted via the coupling member 316 to a personal mobile processing device (not shown), for example, for further processing.

In the example embodiment, optionally, a pressure detection assembly 318 may be provided in the optical measurement device 300. The pressure detection assembly 318 can be configured to detect and transmit to a personal mobile processing device (not shown) an amount of pressure applied by a body part of a user to the measurement device 300 during optical measurement. The pressure information can be used, for example but not limited to, to detect whether a body part has been placed on the measurement device and/or whether the pressure exerted by a body part is sufficient for accurate readings to be obtained.

The optical measurement device 300 can additionally be integrated with optical filters e.g. 320 to minimize the disturbance from ambient light. In the example embodiment, an edge filter with optical transmission characteristics can be used.

FIG. 3(c) is a diagram illustrating optical transmission characteristics of optical filtering in an example embodiment. In this example embodiment, wavelengths of light below about 600 nm is filtered out and prevented from reaching the light detectors e.g. 314. This can be effective as the wavelengths of interest are that of e.g. about 600 nm and about 940 nm only. Alternatively, filters which target specific wavelengths of interest can be used. For example, filters which, e.g. when used in combination, allow transmission of light from about 600-700 nm, and about 900-1000 nm can be used. Alternatively, a single filter which allow transmission of light from about 600-1000 nm can be used alone.

Figure 4:
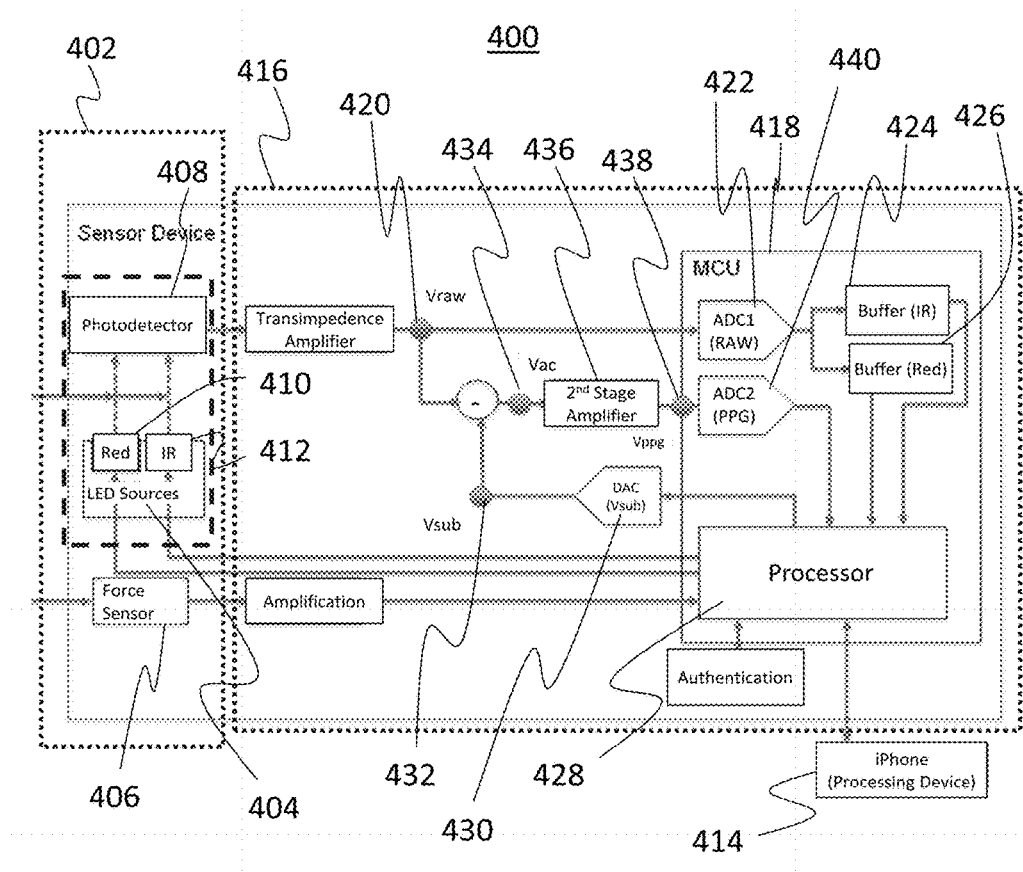
FIG. 4 is a schematic diagram illustrating an optical measurement device being coupled to a personal mobile processing device in an example embodiment.

FIG. 4 is a schematic diagram illustrating an optical measurement device 400 being coupled to a personal mobile processing device in an example embodiment. The optical measurement device 400 functions substantially identical to the measurement device 300 described with reference to FIGS. 3(a) and (b). The optical measurement device 400 comprises a sensing portion 402 that in turn comprises an illumination and detection assembly 404 and optionally, a pressure detection assembly or pressure/force sensing portion 406. The illumination and detection assembly 404 comprises one or more photodetectors e.g. 408, a red LED light source 410 and an infra-red LED light source 412. The measurement device 400 is shown coupled to the personal mobile processing device 414 which can be, for example but not limited to, an Apple® iPhone® (Apple Computer, Inc., Cupertino, Calif.).

A processing module 416 of the optical measurement device 400 is exploded for better illustration. The functions of the processing module 416 can be provided by hardware and/or firmware of the optical measurement device 400.

In use, after establishing a physical connection of the illumination and detection assembly 404 with the personal mobile processing device 414, a microcontroller unit (MCU) 418 in the optical measurement device 400 can extract information for authentication purposes prior to sending of data to the personal mobile processing device 414. This authentication process may be specific to the iPhone®, as Apple® requires that any device using the 30 pin connector purchase an authentication token from Apple®. It will be appreciated that variations or elimination of the above process is possible depending on the personal mobile processing device 414.

With the example of an iPhone®, communication is enabled via the Universal Asynchronous Receiver/Transmitter (UART) protocol from the 30 pin connector of the iPhone®. Strings of data are sent to UART every 8 milliseconds from the MCU 418 to the iPhone®.

In the example embodiment, the data is comprised of 2 bytes of header and 10 bytes of payload. The payload is sub-divided into 5 parts, each comprising 2 bytes of data, i.e. DC1 (IR), DC2 (Red), PPG1 (IR), PPG2 (Red) and FS (Force Sensor). This data is obtained in a HEX file format and is then converted to back to voltage (V). It will be appreciated that variations of the data/payload is possible depending on the desired application, for example, whether or not the force sensing portion 406 is included in the device 400.

With reference to FIG. 1, DC1 and DC2 provide information for the DC component 104 of a PPG waveform, thus enabling calculation for saturation of peripheral oxygen, or $SpO_2$. PPG1 and PPG2 establish an actual PPG waveform and provide information for the AC component 102 of the PPG waveform. Optionally, FS sets out to provide information of the amount of pressure applied to the illumination and detection assembly 404. An example of the data decoding format is show in Table 1 below.

TABLE 1

Data Decoding Format

| Time (ms) | Data from Device | DC1 (Hex) | DC2 (Hex) | PPG1 (Hex) | PPG2 (Hex) | FS (Hex) | DC1 (V) | DC2 (V) | PPG1 (V) | PPG2 (V) | FS (V) |
|---|---|---|---|---|---|---|---|---|---|---|---|
| 0 | F0E20A01023A01F00350055E | 0701 | 023A | 01F0 | 0350 | 055E | 2.8905 | 0.9189 | 0.7996 | 1.3671 | 2.2150 |
| 8 | F0E20A01023A02A80347056D | 0701 | 023A | 02A8 | 0347 | 056D | 2.8905 | 0.9189 | 1.0962 | 1.3526 | 2.2392 |
| 16 | F0E20A01023A031802B7057A | 0701 | 023A | 0318 | 02B7 | 057A | 2.8905 | 0.9189 | 1.2768 | 1.1204 | 2.2602 |
| 24 | F0E20A01023A0314026D0584 | 0701 | 023A | 0314 | 026D | 0584 | 2.8905 | 0.9189 | 1.2703 | 1.0011 | 2.2763 |
| 32 | F0E20A01023A029E02D0058C | 0701 | 023A | 029E | 02D0 | 058C | 2.8905 | 0.9189 | 1.0801 | 1.1607 | 2.2892 |
| 40 | F0E20A01023A01E303550591 | 0701 | 023A | 01E3 | 0355 | 0591 | 2.8905 | 0.9189 | 0.7787 | 1.3751 | 2.2973 |
| 48 | F0E20A01023A012D03400592 | 0701 | 023A | 012D | 0340 | 0592 | 2.8905 | 0.9189 | 0.4852 | 1.3413 | 2.2989 |
| 56 | F0E20A01023A00C402AE0591 | 0701 | 023A | 00C4 | 02AE | 0591 | 2.8905 | 0.9189 | 0.3160 | 1.1059 | 2.2973 |
| 64 | F0E20A01023A00D0026E058D | 0701 | 023A | 00D0 | 026E | 058D | 2.8905 | 0.9189 | 0.3353 | 1.0027 | 2.2908 |
| 72 | F0E20A01023A014D02DB0585 | 0701 | 023A | 014D | 02DB | 0585 | 2.8905 | 0.9189 | 0.5368 | 1.1785 | 2.2779 |
| 80 | F0E20A01023A0209035A057B | 0701 | 023A | 0209 | 035A | 057B | 2.8905 | 0.9189 | 0.8399 | 1.3832 | 2.2618 |
| 88 | F0E20A01023A02BC0338056E | 0701 | 023A | 02BC | 0338 | 056E | 2.8905 | 0.9189 | 1.1285 | 1.3284 | 2.2408 |
| 96 | F0E20A01023A031F02A5055F | 0701 | 023A | 031F | 02A5 | 055F | 2.8905 | 0.9189 | 1.2881 | 1.0914 | 2.2167 |
| 104 | F0E20A01023A030B0270054E | 0701 | 023A | 030B | 0270 | 054E | 2.8905 | 0.9189 | 1.2558 | 1.0060 | 2.1893 |
| 112 | F0E20A01023A028802E5053B | 0701 | 023A | 0288 | 02E5 | 053B | 2.8905 | 0.9189 | 1.0447 | 1.1946 | 2.1586 |
| 120 | F0E20A01023A01F00350055E | 0701 | 023A | 01C9 | 035E | 0526 | 2.8905 | 0.9189 | 0.7367 | 1.3896 | 2.1248 |

Turning to FIG. 4, in the example embodiment, the LEDs 410, 412 illuminate a user's part or surface portion for measurement. A raw PPG signal is detected at the photodetector 408.

A raw PPG signal includes DC and AC components, both of which contain information for waveform analysis. Signal conditioning is therefore performed to obtain the information for further processing at the personal mobile processing device 414. An exemplary signal conditioning process is described below.

To determine the DC component of the PPG signal, a raw signal 420 obtained from the photodetector 408 is digitized at an Analog-to-Digital converter (ADC1) 422. The digitized signal is passed on to both a infra-red buffer (IR) 424 and a red buffer (Red) 426 accordingly, which can each store up to 100 samples before sending collated data to a processor 428.

Using the raw samples, a baseline DC component can be determined by the processor 428. At the processor 428, the digital values for Vsub (IR) and Vsub (RED) (i.e. the DC components) are calculated. The Vsub signals are subsequently converted by a digital-to-analog converter (DAC) 430 to provide resultant digital Vsub signals 432.

The determined DC component (Vsub) 432 is then subtracted from the raw signal, Vraw (at numeral 420) to obtain Vac 432. The new raw signal, Vac 432, then undergoes a second stage amplification at a second stage amplifier 436 to obtain Vppg 438, where the signal to noise ratio is improved as compared with Vraw 420.

The resolution of the new raw signal Vppg 438 is enhanced substantially when digitized at an Analog-to-Digital converter ADC2 440.

Figures 5A, 5B, 5C:
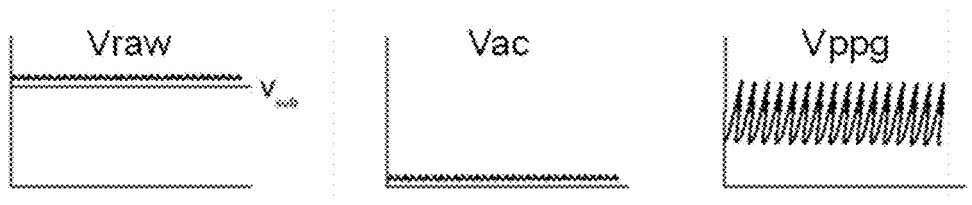
FIGS. 5(a) to (c) are schematic graphical representations of a Vraw signal, a Vac signal and a Vppg signal respectively in an example embodiment.

FIGS. 5(a) to (c) are schematic graphical representations of a Vraw signal, a Vac signal and a Vppg signal respectively in an example embodiment. A determined DC component Vsub is subtracted from a raw signal Vraw to obtain a Vac signal. The new raw signal Vac then undergoes a second stage amplification at a second stage amplifier to obtain a Vppg signal, where the signal to noise ratio is improved as compared with the Vraw signal from FIG. 5(a).

Figure 6:
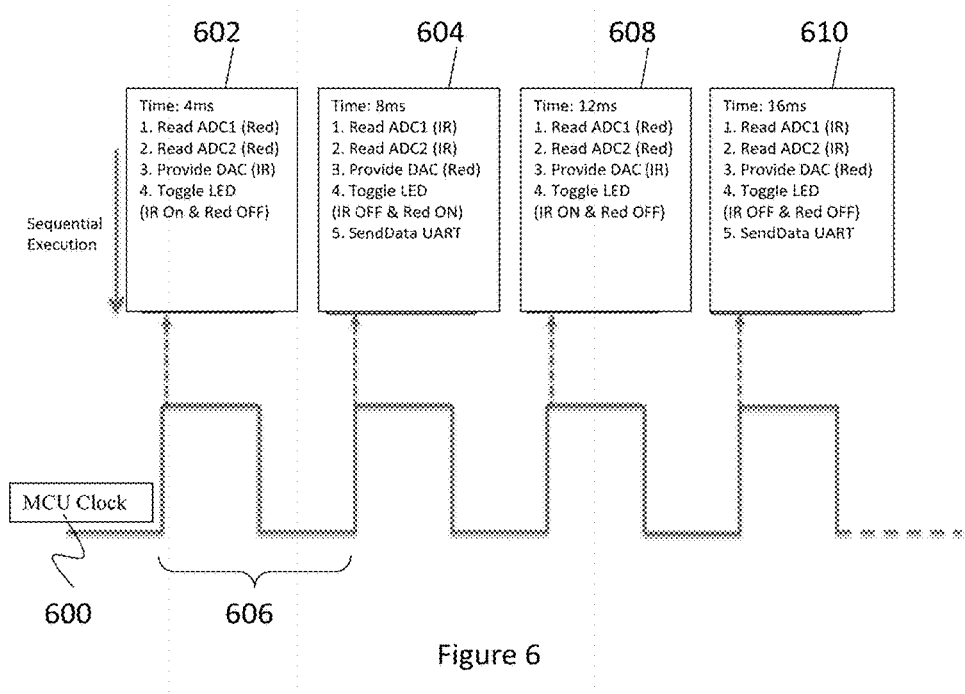
FIG. 6 is a schematic illustration of a time waveform for collecting data from infra-red and red light illumination in an example embodiment.

FIG. 6 is a schematic illustration of a time waveform for collecting data from infra-red and red light illumination in an example embodiment. Reference is made to components of FIG. 4. An MCU clock 600 of the MCU 418 is set to toggle at a predetermined interval to accommodate retrieving results from both LED (IR) 412 and LED (RED) 410 during a respective first interval 602 and second interval 604. In the example embodiment, the interval 606 is set to 4 milliseconds. The data collection sequence is then repeated in the third interval 608 and fourth interval 610 etc. Before each toggle between the two LEDs 410, 412, data from ADC1 422 and ADC2 440 are taken and sent to the UART to the personal mobile processing device 414, for example, for further processing.

Therefore, in the above described example embodiment, an illumination and detection assembly and preferably, a pressure detection assembly, may be integrated as a single, compact optical measurement device surrounded by a housing for portable use. Thus, the housing can provide structural rigidity as compared to e.g. conventional plaster-type devices. The optical measurement device is substantially non-deformable and can comprise a substantially non-adhesive measurement surface.

The optical measurement device can be provided without a holder or clip or cuff, i.e. the measurement device is holderless. Further, a measurement surface can be provided for the measurement device such that a user can access the measurement surface using a surface portion, such as a finger tip of the user, for measurement. With the measurement device being holderless, the surface portion of the user can access the measurement surface from all directions in a single plane. The single plane may be on a same plane as the measurement surface.

Furthermore, detected light information can be transmitted to another device, for e.g. the feedback unit/personal mobile processing device, to carry out further processing. Thus, the measurement device is not processor-intensive, e.g. may not require a processor, and can therefore function without a dedicated power supply such as a battery. Thus, the measurement device can be manufactured to be relatively small as compared to conventional devices.

It is appreciated that the detected light information or Vppg signal transmitted to the personal mobile processing device has a substantial extent of ambient light interference. Therefore, ambient light or noise cancellation is performed at the personal mobile processing device. The description below relating to ambient noise cancellation for SPO2 calculations can be implemented through software and/or hardware modules. The hardware modules can comprise electronic circuitry or dedicated application chips such as an ASIC chip. A graphical user interface (GUI) may be provided, such as an "app" or software application on a smartphone, to be run on the personal mobile processing device to implement and display the ambient noise cancellation.

To determine SpO2 values, for example, a proprietary lookup table is typically provided by manufacturers. A calculated ratio R is used for referring to the lookup table to determine SpO2 values.

R is defined as, $$R = \frac{\frac{AC_R}{DC_R}}{\frac{AC_{IR}}{DC_{IR}}}$$

where AC, DC refer to alternating current and direct current values respectively. The conditions IR and R refer to conditions whereby infra-red light and red light are used respectively. It is noted that ambient light noise is usually subtracted or removed in the R calculations.

In example embodiments, there can be provided a method and system for noise cancellation, e.g. for SpO2 measurements. In one example embodiment, AC and DC values are respectively obtained for a Red PPG signal measurement, an IR PPG signal measurement and an ambient PPG signal measurement (where both the red and IR LEDs are turned off). The maximum and minimum values of the PPG signal measurements are determined. A SpO2 value based on a ratio R value calculated using the determined maximum and minimum values can then be determined.

Advantageously, in the example embodiment, a signal reconstruction of true Red and/or IR PPG signals to remove ambient signal interference can be avoided. The inventors have recognised that by identifying and utilising only significant information for SpO2 calculation, an efficient and accurate calculation can be carried out. The inventors have recognized that by using only the maximum and minimum values of the respective red, IR and ambient signal pulses, the calculation of SpO2 can be carried out. For example, a maximum of the true Red PPG signal (devoid of ambient noise) can simply be obtained by subtracting the obtained maximum value of the Red PPG signal, obtained when the Red LED is turned on, with the obtained maximum value of the ambient PPG signal, i.e. when none of the LEDs is turned on.

In other words, instead of reconstructing a true Red PPG signal (devoid of ambient signal) and a true IR PPG signal (devoid of ambient signal), advantageously, reconstruction is avoided in example embodiments, and only the maximum and minimum values of 3 PPG signals are obtained for analysis to obtain SpO2 value. This can minimise processing and consume less power.

A feedback unit/personal processing device can be provided for removal of ambient noise signal from an optical measurement in an example embodiment. The device can comprise a coupling member e.g. for coupling to an optical measurement device. The coupling member can receive a first signal waveform obtained based on detecting light based on a first light illumination, a second signal waveform obtained based on detecting light based on a second light illumination, and a third signal waveform obtained based on detecting ambient light. The device can also comprise a processor module that can obtain respective maximum and minimum values of at least two of the first, second and third signal waveforms; and the processor can derive signal values of the first and second signal waveforms with the removal of ambient noise by using the maximum and minimum values of at least two of the first, second and third signal waveforms.

FIGS. 4, 5 and 6 can relate to one or more example implementations/applications of e.g. the optical measurement device 300. FIGS. 7 to 21 can provide further example implementations/applications of the optical measurement device. It will be appreciated by a person skilled in the art that the methods or algorithms etc. described may have steps or components which may be used in combination or in place of each other.

Figure 7:
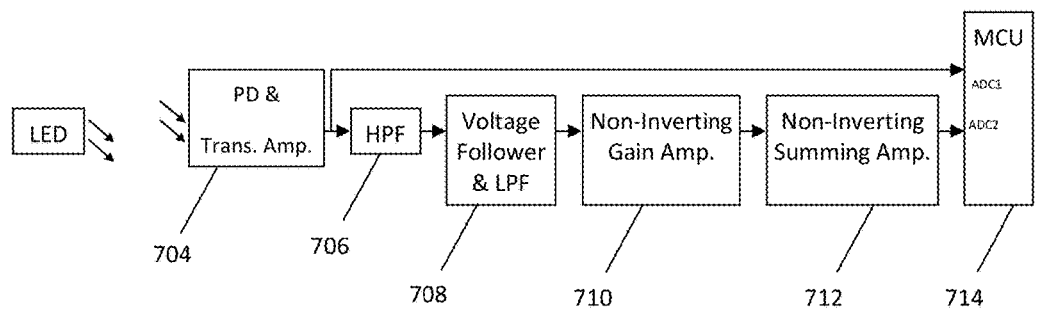
FIG. 7 is a schematic block diagram illustrating circuitry for obtaining information for SpO2 calculation in an example embodiment.

FIG. 7 is a schematic block diagram illustrating circuitry for obtaining information for SpO2 calculation in an example embodiment. The circuitry is provided in an optical measurement device that is external a personal mobile processing device. At block 704, the photodetector (compare 408 FIG. 4) coupled to a transimpedance amplifier is arranged to detect light information. These components are coupled a high-pass filter module 706 that is in turn coupled to a voltage follower module 708. The voltage follower module 708 is coupled to a non-inverting amplifier module 710 that is in turn coupled to a non-inverting summing amplifier module 712. An output of the non-inverting summing amplifier module 712 is coupled to ADC2 of a MCU 714 (compare 440, 418 FIG. 4). Further, an output of block 704 is coupled to ADC1 of the MCU 714 (compare 422, 418 FIG. 4).

Figure 8:
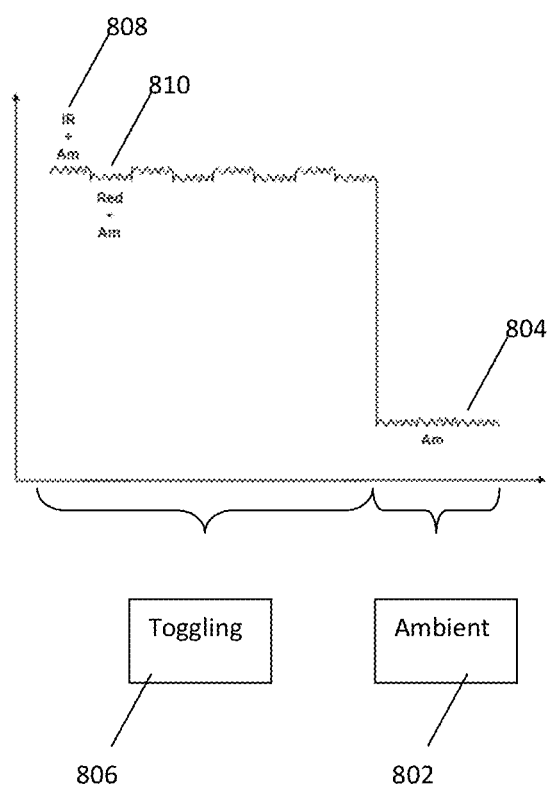
FIG. 8 is a schematic graphical illustration of output obtained at a light detector during a light emitting diode (LED) firing sequence in an example embodiment.
Figure 9:
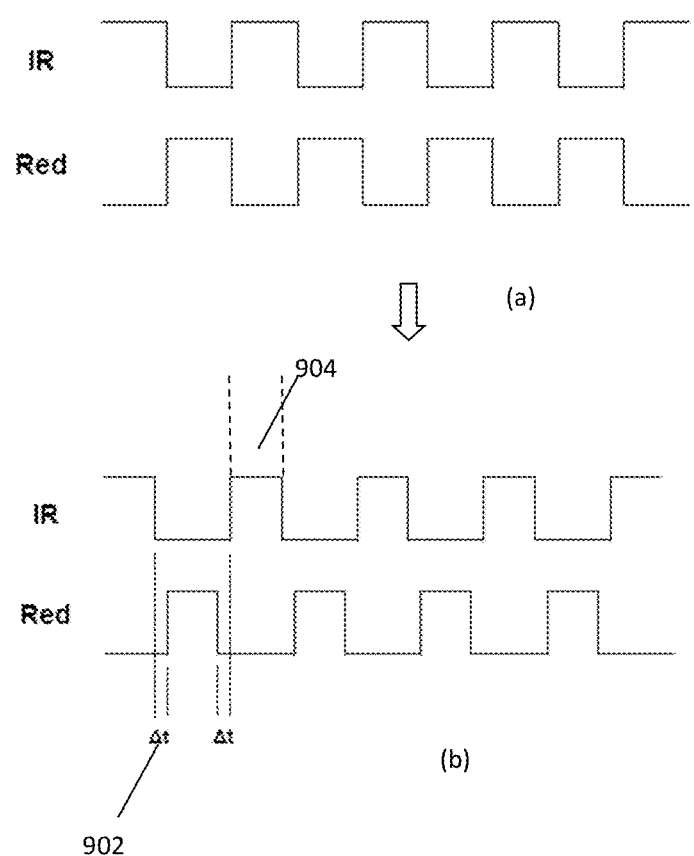
FIG. 9(a) is a schematic timing wave diagram for toggling on/off of an infra-red (IR) LED and a red (Red) LED in an example embodiment.
FIG. 9(b) is an alternative schematic timing wave diagram for toggling on/off of an IR LED and a Red LED in an example embodiment.
Figure 10:
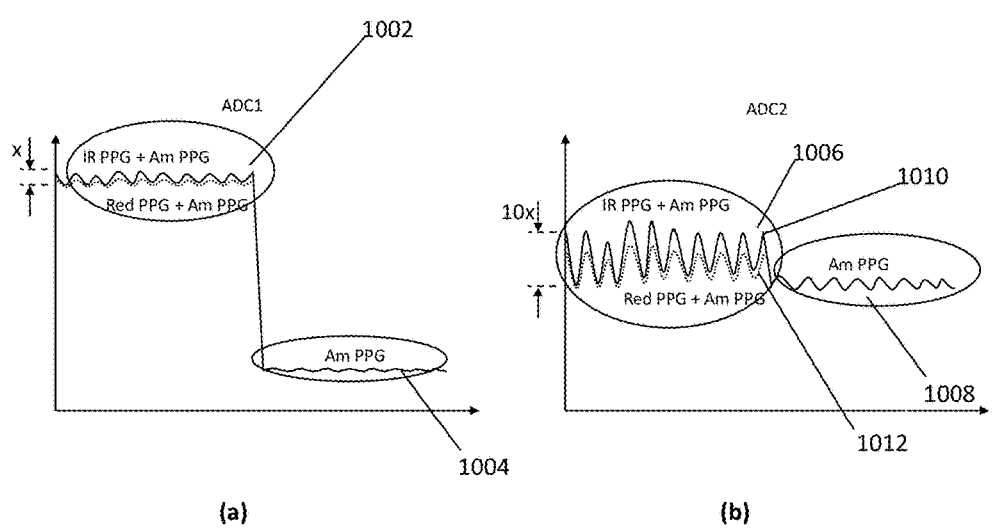
FIG. 10(a) is a graph schematically illustrating signals acquired at an analog to digital converter in an example embodiment.
FIG. 10(b) is a graph schematically illustrating alternating current (AC) signals acquired at an analog to digital converter in an example embodiment.
Figure 11:
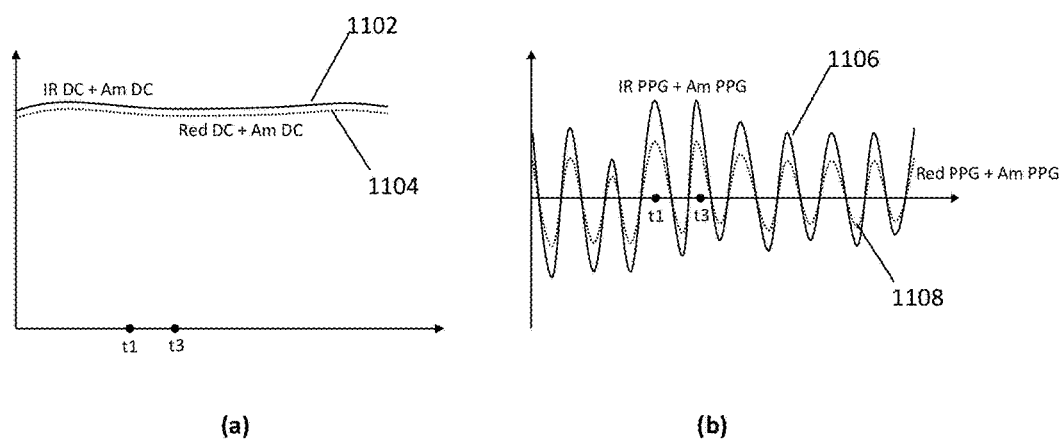
FIG. 11(a) is a graph schematically illustrating filtered DC signals in an example embodiment.
FIG. 11(b) is a graph schematically illustrating filtered AC signals in an example embodiment.

FIG. 8 is a schematic graphical illustration of output obtained at a light detector (compare 704 of FIG. 7) during a light emitting diode (LED) firing sequence in an example embodiment. During an Ambient (Am) or OFF condition 802, both the IR and RED LEDs are turned off, and an ambient PPG signal 804 can be obtained. During a toggling sequence 806, the IR and RED LEDs are alternatingly turned on. The MCU can then perform time based de-multiplexing to extract the respective IR and RED PPG signals. An example of de-multiplexed signals can be observed in FIG. 11(b). The IR PPG signals (in bold) and Red PPG signals (dotted) can be obtained. Another example of de-multiplexed signals can be provided whereby individual sampled points are represented, rather than the complete waveforms formed by the individual points.

FIG. 9(a) is an exemplary schematic timing wave diagram for toggling on/off of an IR LED and a Red LED. FIG. 9(b) is an alternative schematic timing wave diagram for toggling on/off of an IR LED and a Red LED in an example embodiment. FIG. 9(b) is a modification of FIG. 9(a) to allow an ambient PPG signal to be obtained. FIG. 9(b) also illustrates a toggling sequence within sequence 806 of FIG. 8. There is a relatively brief period Δt 902 between each toggling, e.g. about 100 μs, when both the Red and IR LEDs are turned off. Each LED is turned on for about 2.9 ms e.g. numeral 904, which makes each toggling cycle to be about 6 ms. This can improve the IR and Red PPG signals accuracy. The brief period Δt 902 allows a time break between switching from a Red and IR signal condition (or vice versa). This may be useful to a single path system whereby detection of the red and IR signals are performed using the same circuitry. The brief period Δt 902 introduced can ensure that each detected Red and IR light information displays its own behavior. The inventors have recognised that if there is no break e.g. provided by period Δt 902, the light signal of the previously switched on LED may still be present in the processing path. That is, using the brief period can reduce "crosstalk" issues.

In some example embodiments, the intensity of each IR and Red LED is further tuned such that the output at the photodetector shows a response of between 2V-2.5V (at ADC1). That is, the inventors have recognized that the effects of ambient light signals can be reduced as much as possible by tuning the intensities of the IR and Red LEDs to be maximized as long as the photodetector has not reached saturation. In the example embodiment, the saturation voltage is based on the Vcc used and is about 3.3V.

Thus, the inventors have recognized that ambient light interference can be minimized as compared to the IR and Red signals detected. Thus, in the example embodiment, detection of the ambient signal can be conducted in its own ambient detection period before or after the toggling sequence of the IR and Red light sources.

Returning to FIG. 7, the output from block 704 is transmitted to the high-pass filter module 706 and in turn to the voltage follower module 708 to remove the DC component from the PPG signal. The remaining AC component is amplified by the non-inverting amplifier module 710 to maximize the peak-to-peak amplitude of the PPG signal. In an example embodiment, the AC component is amplified to about 0-3.3V with a gain of about 10-40 times. Thereafter, a non-inverting summing amplifier 712 introduces an arbitrary DC component to the AC signal such that the signal oscillates about the arbitrary DC value.

As seen in FIG. 7, ADC1 provides the DC portion of the measured signal and ADC2 provides the AC portion of the measured signal.

FIG. 10(a) is a graph illustrating signals acquired at an analog to digital converter (compare ADC1 of FIG. 7) in an example embodiment. The y-axis is in terms of mV and the x-axis is in terms of ms. Numeral 1002 shows the signals obtained when the Red and IR LEDs are turned on during the toggling sequence 806 (FIG. 8). Numeral 1004 shows the signals obtained when the Red and IR LEDs are turned off during the OFF condition 802 (FIG. 8). As shown, the amplitude of the signals obtained during the toggling sequence 806 (FIG. 8) is notated as x'.

FIG. 10(b) is a graph illustrating AC signals acquired at an analog to digital converter (compare ADC2 of FIG. 7) in an example embodiment. The y-axis is in terms of mV and the x-axis is in terms of ms. Numeral 1006 shows the AC signals when the Red and IR LEDs are turned on during the toggling sequence 806 (FIG. 8). Numeral 1008 shows the AC signals when the Red and IR LEDs are turned off during the OFF condition 802 (FIG. 8). The IR signals are shown with solid lines at 1010 and the Red signals are shown with dotted lines at 1012. With the amplification provided in FIG. 7, as shown, the difference between the Red and IR detected AC signals is notated as 10x', i.e. a gain of about 10 times has been provided.

The IR condition refers to when only the IR LED is turned on, while the Red condition refers to when only the Red LED is turned on. The IR and/or the Red conditions are illustrated in FIGS. 9(a) and 9(b). That is, even if the brief time period Δt 902 is included, the respective condition, Red or IR, is still relevant given the longer preceding amount of time when one of the LEDs is turned on. The ambient condition refers to when none of the LEDs are turned on, and the signal is obtained due to the ambient light conditions. See numeral 802 of FIG. 8.

With the AC and DC signal portions, the inventors have recognised that significant information can be further extracted for SpO2 calculation. Using the circuit of FIG. 7, it can be seen from FIGS. 10(a) and (b) that the AC and DC components of the Red and IR PPG signals are larger than those of the ambient PPG signal. Therefore, the contribution of the ambient PPG signal is less significant compared with the contribution of the RED or IR PPG signals. This can provide for a more accurate SpO2 calculation. That is, in example embodiments, the LED illumination intensity can be tuned to a level that provides for detected signals that provide as high a detected voltage as possible, without saturating the signals. The intensity can be controlled by the MCU. The tuning can ensure that both Red and IR signals transmitted to ADC1 can reach an amplitude level significantly higher than Ambient signals transmitted to ADC1. For example, if an Ambient signal at ADC1 is about 0.5V, both Red and IR signals at ADC1 can preferably be set at about 2V or above. This is described and illustrated in more detail below with FIG. 18. In addition, there can be steps taken to ensure that detected Ambient light signals are not too high. Exemplary steps are described and illustrated in more detail below with FIG. 17(b).

Based on the LED firing sequence as illustrated in FIG. 8, the data obtained at ADC1 and ADC2 can be processed to select the AC and DC components of the IR, Red and Ambient conditions.

The signals shown in FIGS. 10(a) and (b) can undergo further digital signal processing steps. The modules for such processing may not be all shown in FIG. 7. In the example embodiment, the DC data is passed through a low pass filter (e.g. filtering>0.8 Hz) and the AC data can be passed through a band pass filter (e.g. filtering<0.5 Hz and >30 Hz) (not shown in FIG. 7).

FIG. 11(a) is a graph illustrating filtered DC signals in an example embodiment. The y-axis is in terms of mV and the x-axis is in terms of ms. The graph shows filtered DC signals of when the Red and IR LEDs are turned on during the toggling sequence 806 (FIG. 8). The IR signals are shown with solid lines at 1102 and the Red signals are shown with dotted lines at 1104.

FIG. 11(b) is a graph illustrating filtered AC signals in an example embodiment. The y-axis is in terms of mV and the x-axis is in terms of ms. The graph shows filtered AC signals of when the Red and IR LEDs are turned on during the toggling sequence 806 (FIG. 8). The IR signals are shown with solid lines at 1106 and the Red signals are shown with dotted lines at 1108.

FIG. 12(a) is a graph illustrating filtered DC signals for an ambient PPG signal in an example embodiment. The y-axis is in terms of mV and the x-axis is in terms of ms. The graph shows filtered DC signals 1202 when the Red and IR LEDs are turned off during the OFF condition 802 (FIG. 8).

FIG. 12(b) is a graph illustrating filtered AC signals for an ambient PPG signal in an example embodiment. The y-axis is in terms of mV and the x-axis is in terms of ms. The graph shows filtered AC signals 1204 when the Red and IR LEDs are turned off during the OFF condition 802 (FIG. 8).

From FIGS. 11(b) and 12(b), the maximum and minimum points for each cycle, and the corresponding data and time for those maximum and minimum points are identified, see t1 and t3. It will be appreciated that the maximum and minimum values can be obtained using any peak detection techniques.

FIG. 13(a) is an enlarged version of FIG. 11(a), focusing on a specific period between $t_1$ to $t_3$ of the filtered DC signal. The IR signals are shown with solid lines at 1302 and the Red signals are shown with dotted lines at 1304.

FIG. 13(b) is an enlarged version of FIG. 11(b), focusing on a specific period between $t_1$ to $t_3$ of the filtered AC signal. The IR signals are shown with solid lines at 1306 and the Red signals are shown with dotted lines at 1308. The maximum point data at t1 and t3 are identified as IR1, R1, IR3, R3 accordingly. See numerals 1310, 1312 respectively. The minimum point data at t2 is identified as IR2, R2. See numeral 1314.

Figure 12:
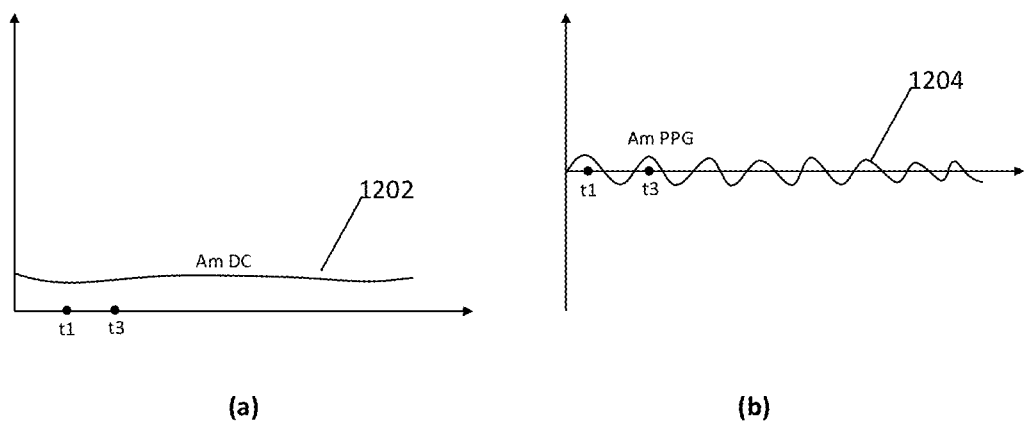
FIG. 12(a) is a graph schematically illustrating filtered DC signals for an ambient PPG signal in an example embodiment.
FIG. 12(b) is a graph schematically illustrating filtered AC signals for an ambient PPG signal in an example embodiment.
Figure 14:
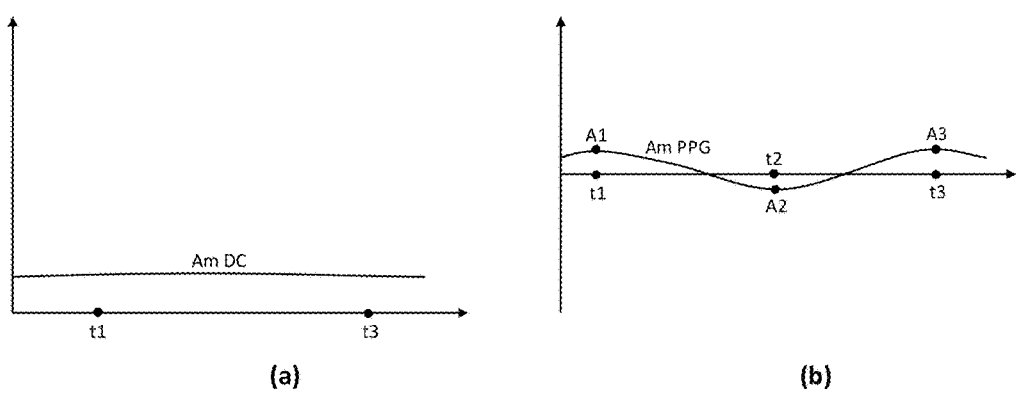
FIG. 14(a) is an enlarged version of FIG. 12(a).
FIG. 14(b) is an enlarged version of FIG. 12(b).
Figure 15:
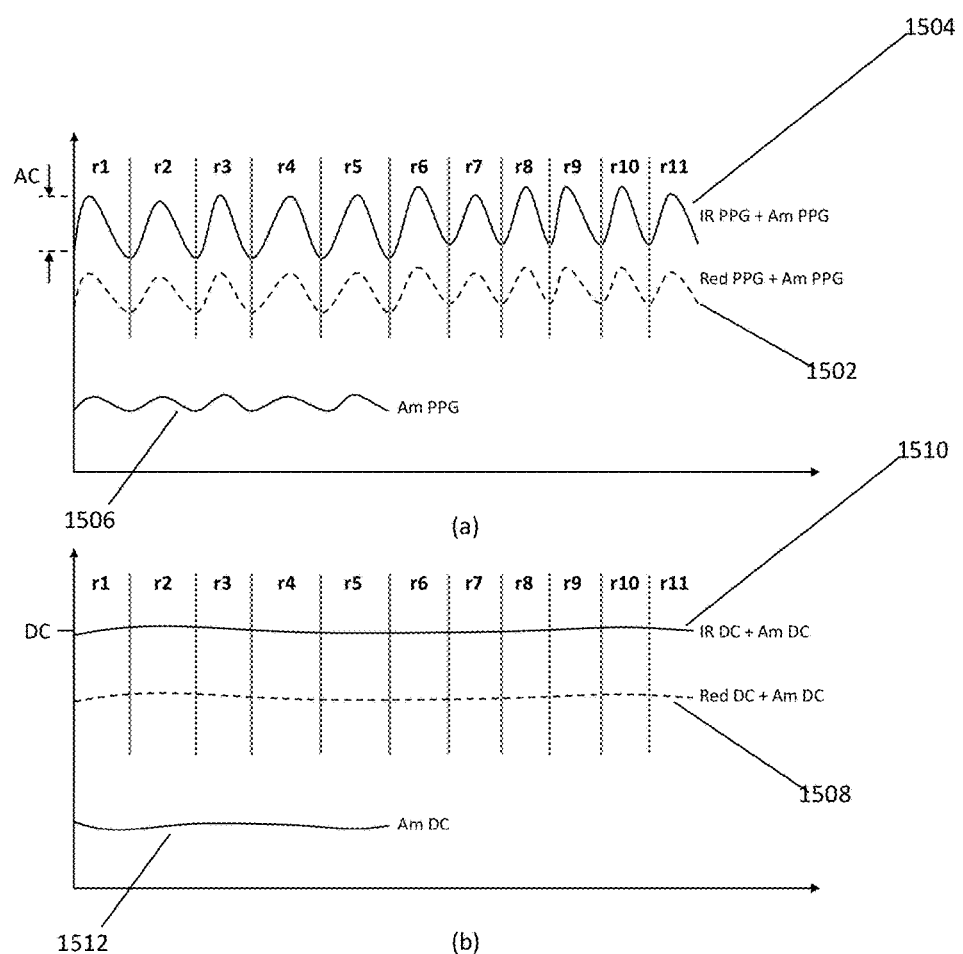
FIG. 15 is a schematic graph illustrating PPG signals obtained for a plurality of cycles in an example embodiment.

FIG. 14(*a*) is an enlarged version of FIG. 12(*a*) focusing on a specific period between t1 to t3 of the filtered DC signal.

FIG. 14(*b*) is an enlarged version of FIG. 12(*b*), focusing on a specific period between t1 to t3 of the filtered AC signal. The maximum point data at t1 and t3 are identified as A1, A3 accordingly. The minimum point data at t2 is identified as A2.

It should be noted that the notations such as t1, t2, t3 are arbitrary notations for signifying three timings and are not the same when referred to for an IR condition, a Red condition and an Ambient condition.

It will be appreciated that in an ideal situation, e.g. with individual photodetectors and signal paths for all 3 conditions (IR, Red and Ambient), and perfectly noise free conditions, all peaks and troughs may in theory occur at the same points. In other words, t1, t2 and t3 are the same when referring to the various conditions. In the present examples, because a single path is utilized, a peak sampled during the IR condition cannot be simultaneously measured for the R condition. As such, there are minor differences in peak and trough, e.g. t1, t2 and t3, times. If sampling is on a basis of IR, Red and Ambient conditions i.e. one sample per condition, it can be expected that the peaks and troughs of the respective signals (IR, R and Ambient), e.g. at t1, t2 and t3, may only be one sample off from each other. If the timings are too far off of each other (e.g. 2 or more samples apart), the particular set of samples can be rejected from the calculations if desired.

In the presently described example embodiments, as there are toggling and ambient phases (e.g. 806 and 802 of FIG. 8), the ambient signal peaks and troughs cannot be obtained at the same time as the R and IR peaks and troughs. As such, individual signals for IR, R and ambient conditions are "reconstructed" and analysed separately. This can also be extended to a 3 phase sequence, e.g. IR condition on for 15 seconds, R condition on for 15 seconds and ambient condition on for 15 seconds.

Figure 13:
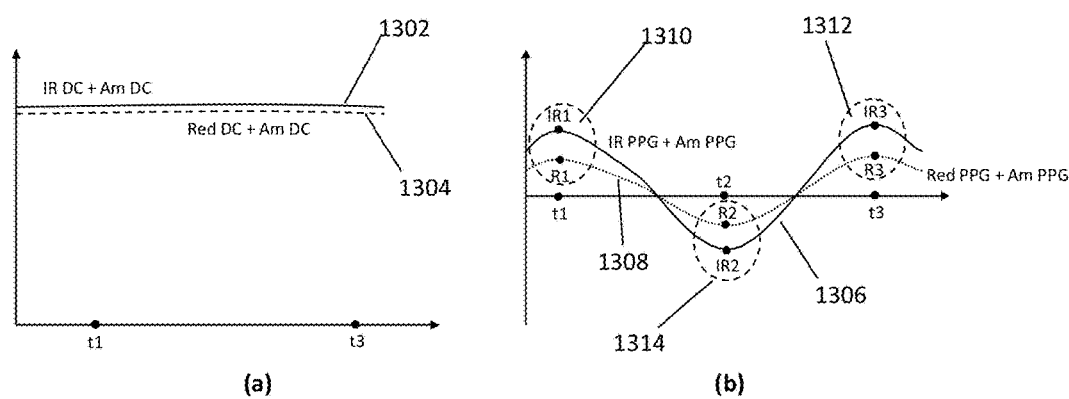
FIG. 13(a) is an enlarged version of FIG. 11(a).
FIG. 13(b) is an enlarged version of FIG. 11(b).

With the information from FIGS. 13(*a*), 13(*b*), 14(*a*) and 14(*b*), a ratio R can be calculated by the following:

$$DC_{IR} + DC_{Am} = \frac{\sum_{t3}^{t1} DC_{IR+Am}}{n_{t1-t3}} \times \text{Gain}$$

$$DC_R + DC_{Am} = \frac{\sum_{t3}^{t1} DC_{R+Am}}{n_{t1-t3}} \times \text{Gain}$$

$$DC_{Avg.Am} = \frac{\sum_{i_{cycle}} \left( \frac{\sum_{t3}^{t1} DC_{Am}}{n_{t1-t3}} \right)}{i_{cycle}} \times \text{Gain}$$

$$AC_{IR} + AC_{Am} = \frac{(IR1 + IR3)}{2} - IR2$$

$$AC_R + AC_{Am} = \frac{(R1 + R3)}{2} - R2$$

$$AC_{Avg.Am} = \frac{\sum_{i_{cycle}} \left( \frac{(A1 + A3)}{2} - A2 \right)}{i_{cycle}}$$

where $DC_{IR}+DC_{Am}$ is the DC value of one cycle of the IR LED being turned on during the toggle sequence 806 (FIG. 8); $n_{t1-t3}$ is the number of sampling points within the t1 to t3 time frame, i.e. an average of the values is being obtained (for DC measurements); $AC_{IR}+AC_{Am}$ is the AC value of one cycle of the IR LED being turned on during the toggle sequence 806 (FIG. 8); $DC_R+DC_{Am}$ is the DC value of one cycle of the Red LED being turned on during the toggle sequence 806 (FIG. 8); $AC_R+AC_{Am}$ is the AC value of one cycle of the Red LED being turned on during the toggle sequence 806 (FIG. 8); $DC_{avg,Am}$ is the average DC value of the ambient signal detected during the OFF condition 802 (FIG. 8); $i_{cycle}$ is the number of cycles taken for analysis and $AC_{avg,Am}$ is the average AC value of the ambient signal detected during the OFF condition 802 (FIG. 8). The gain is set to be the same when both LEDs are turned ON. Therefore, during calculations, the gain value cancels out and therefore can be set as any arbitrary value.

The inventors have recognised that the relationship between light intensity (I) and amplitude (A) is as follows:

$$I \alpha A^2$$

$$I = kA^2$$

Hence, $$I_{signal} = I_{signal+am} - I_{am}$$

$$kA_{signal}^2 = kA_{signal+am}^2 - kA_{am}^2$$

$$A_{signal} = \sqrt{A_{signal+am}^2 - A_{am}^2}$$

Therefore, using the intensity to amplitude relationship above, where $A_{am}^2$ is substituted with $DC_{Avg,Am}^2$, and the $A_{signal+am}^2$ is respectively substituted with the square of average values over an $i_{cycle}$ of the respectively DC or AC calculations from the set of equations above.

$$DC_{IR} = \sqrt{\left( \frac{\sum_{i_{cycle}} (DC_{IR} + DC_{Am})}{i_{cycle}} \right)^2 - DC_{Avg.Am}^2}$$

$$DC_R = \sqrt{\left( \frac{\sum_{i_{cycle}} (DC_R + DC_{Am})}{i_{cycle}} \right)^2 - DC_{Avg.Am}^2}$$

$$AC_{IR} = \sqrt{\left( \frac{\sum_{i_{cycle}} (AC_{IR} + AC_{Am})}{i_{cycle}} \right)^2 - AC_{Avg.Am}^2}$$

$$AC_R = \sqrt{\left( \frac{\sum_{i_{cycle}} (AC_R + AC_{Am})}{i_{cycle}} \right)^2 - AC_{Avg.Am}^2}$$

Typically, $$R = \frac{\frac{AC_R}{DC_R}}{\frac{AC_{IR}}{DC_{IR}}}$$

Thus, in the above described example embodiment, direct-current (DC) and alternating-current (AC) values of a first (e.g. red), second (e.g. IR) and third (e.g. ambient) signal waveforms can be obtained based on the respective maximum and minimum values. The DC and AC values of the third signal waveform can be average values obtained over a plurality of cycles and based on the maximum and minimum values of the third signal waveform. The ratio R can be determined based on using the DC and AC values of the first and second waveforms and the average values obtained from the third signal waveform; and wherein the ratio R is usable for referencing a lookup table.

With the ratio R, SpO2 or the saturation of hemoglobin with oxygen (in blood) can be determined. That is, in some examples, the ratio R can be used to refer to a proprietary lookup table provided by a manufacturer to determine the corresponding SpO2 value. The lookup table can be stored in a database that is in turn loaded onto the personal mobile processing device and the lookup operation is automated.

In example embodiments, optionally, it is possible to determine the quality of the signals so as to inform the user on the accuracy of, for example, a SpO2 measurement.

The quality of a signal can be measured by a propagation error which takes in account the deviation of the 6 parameters used in the calculation of R. i.e.

$$R = f(AC_{ir}, AC_r, AC_{am}, DC_{ir}, DC_r, DC_{am})$$

The inventors have recognised that, indirectly, deviation σR reflects the confidence level of the computation result of R. The calculated propagation error may be displayed on a screen of a personal mobile processing device to inform the user of the potential accuracy of the SpO2 measurement.

Alternatively, instead of the calculated propagation error, a representative description of the propagation error may be displayed. For example, for a propagation error of more than e.g. 30% of the mean of the calculated R, the user may be informed that the measured SpO2 is highly inaccurate and may be advised to retake the readings at a more suitable location. As another example, for a deduced propagation error of less than e.g. 10%, the user may be informed that the measured SpO2 is relatively accurate.

The equations below illustrate the algorithm for determining the accuracy.

$$R = f(AC_{ir}, AC_r, AC_{am}, DC_{ir}, DC_r, DC_{am})$$

$$\sigma_R^2 = \left(\frac{\partial R}{\partial AC_{ir}}\right) \sigma_{AC_{ir}}^2 + \left(\frac{\partial R}{\partial AC_r}\right) \sigma_{AC_r}^2 + \left(\frac{\partial R}{\partial AC_{am}}\right) \sigma_{AC_{am}}^2 +$$

$$\left(\frac{\partial R}{\partial DC_{ir}}\right) \sigma_{DC_{ir}}^2 + \left(\frac{\partial R}{\partial DC_r}\right) \sigma_{DC_r}^2 + \left(\frac{\partial R}{\partial DC_{am}}\right) \sigma_{DC_{am}}^2$$

Further, each parameter has individual deviation as follows, $$DC_{ir} = DC_{avg,ir} + \sigma_{DC_{ir}} \quad AC_{ir} = AC_{avg,ir} + \sigma_{AC_{ir}}$$

$$DC_r = DC_{avg,r} + \sigma_{DC_r} \quad AC_r = AC_{avg,r} + \sigma_{AC_r}$$

$$DC_{am} = DC_{avg,am} + \sigma_{DC_{am}} \quad AC_{am} = AC_{avg,am} + \sigma_{AC_{am}}$$

Hence, the average value of R $$R = \sqrt{\left[\frac{AC_{avg,r}^2 - AC_{avg,am}^2}{DC_{avg,r}^2 - DC_{avg,am}^2}\right] \times \left[\frac{DC_{avg,ir}^2 - DC_{avg,am}^2}{AC_{avg,ir}^2 - AC_{avg,am}^2}\right]}$$

$$\sigma_R =$$

$$R_{avg} \times sqrt \begin{bmatrix} \frac{\sigma_{AC_{ir}}^2}{(AC_{avg,ir} - AC_{avg,am})^2} + \frac{\sigma_{DC_{ir}}^2}{(DC_{avg,ir} - DC_{avg,am})^2} \\ + \frac{\sigma_{AC_r}^2}{(AC_{avg,r} - AC_{avg,am})^2} + \frac{\sigma_{DC_r}^2}{(DC_{avg,r} - DC_{avg,am})^2} \\ + \frac{[(AC_{avg,ir} - AC_{avg,am}) - (AC_{avg,r} - AC_{avg,am})]^2 [\sigma_{AC_{am}}^2]}{(AC_{avg,ir} - AC_{avg,am})^2 (AC_{avg,r} - AC_{avg,am})^2} \\ + \frac{[(DC_{avg,r} - DC_{avg,am}) - (DC_{avg,ir} - DC_{avg,am})]^2 [\sigma_{DC_{am}}^2]}{(DC_{avg,r} - DC_{avg,am})^2 (DC_{avg,ir} - DC_{avg,am})^2} \end{bmatrix}$$

Therefore, it can be derived that $$R = R_{avg} \pm \sigma_R$$

In another example embodiment, the ratio R can be determined using averages of maximum and minimum values. In the example embodiment, each Red and IR PPG signal are paired on a per cycle basis. A subtraction is carried out using an average ambient signal value. The average ambient signal value can be obtained before or after obtaining the Red and IR PPG signals.

FIG. 15(a) is a schematic graph illustrating PPG AC signals obtained for a plurality of cycles in an example embodiment. FIG. 15(b) is a schematic graph illustrating PPG DC signals obtained for a plurality of cycles in an example embodiment. As illustrated as an example, there are 11 cycles shown in FIGS. 15(a) and (b). The Red PPG AC signals over the cycles are shown at numeral 1502, the IR PPG AC signals over the cycles are shown at numeral 1504, and the ambient PPG AC signals are shown at numeral 1506. In FIGS. 15(a) and (b), 11 cycles of IR and RED PPG signals and 5 cycles of ambient PPG signals are shown. This is because the period for obtaining the ambient PPG signals i.e. the ambient phase, is shorter than the toggling phase. It will be appreciated that any number of cycles for each of the signals (Red, IR or ambient) may be used. The Red PPG DC signals over the cycles are shown at numeral 1508, the IR PPG DC signals over the cycles are shown at numeral 1510, and the ambient PPG DC signals are shown at numeral 1512. The ambient PPG DC and AC signals are used to obtain an average ambient signal value avgDC$_{am}$ and avgAC$_{am}$ respectively. In the example embodiment implementing a single path system, the ambient sampling (compare 802) is performed after/before the toggling phase. Therefore, the Ambient signals shown in FIGS. 15(a) and (b) have been time shifted to show aligned cycles with the Red and IR signals, even though they are not necessarily aligned in real time.

A plurality of R values are obtained as follows:

$$R_1 =$$

$$\frac{R_{r1}}{R_{ir1}} = \sqrt{\frac{(AC_{r1}^2 - avgAC_{am}^2)}{(DC_{r1}^2 - avgDC_{am}^2)} \times \frac{(DC_{ir1}^2 - avgDC_{am}^2)}{(AC_{ir1}^2 - avgAC_{am}^2)}} \rightarrow \text{Cycle 1}$$

$$R_2 = \frac{R_{r2}}{R_{ir2}} =$$

$$\sqrt{\frac{(AC_{r2}^2 - avgAC_{am}^2)}{(DC_{r2}^2 - avgDC_{am}^2)} \times \frac{(DC_{ir2}^2 - avgDC_{am}^2)}{(AC_{ir2}^2 - avgAC_{am}^2)}} \rightarrow \text{Cycle 2}$$

↓

↓

-continued $$R_n = \frac{R_{r_n}}{R_{ir_n}} = $$

$$\sqrt{\frac{(AC_{r_n}^2 - avgAC_{am}^2)}{(DC_{r_n}^2 - avgDC_{am}^2)} \times \frac{(DC_{ir_n}^2 - avgDC_{am}^2)}{(AC_{ir_n}^2 - avgAC_{am}^2)}} \rightarrow \text{Cycle } n$$

Therefore, $$R_{avg} = \frac{\Sigma(R_1 + R_2 + \ldots + R_n)}{n}$$

Thus, for the above described example embodiment, direct-current (DC) and alternating-current (AC) values of at least two of the first (e.g. red), second (e.g. IR) and third (e.g. ambient) signal waveforms can be obtained based on the respective maximum and minimum values obtained in one/each cycle. The DC and AC values of the third signal waveform are average values obtained over a plurality of cycles e.g. 11 cycles described above. A ratio R for each cycle (e.g. $R_1$, $R_2$ etc.) can be obtained based on using the DC and AC values of the first and the second signal waveforms and the average values obtained from the third signal waveform. An average R value (e.g. $R_{avg}$) can be obtained based on using the ratio R for a plurality of cycles (e.g. $R_1$, $R_2$ etc.); and wherein the R value (e.g. $R_{avg}$) is usable for referencing a lookup table.

For the calculation of signal quality, the following equation is used.

$$\sigma = \sqrt{\frac{\sum_{i=1}^{n}(R_i - R_{avg})^2}{n}}$$

Therefore, in the above example embodiments for obtaining R, only significant information for SpO2 determination is extracted. This can advantageously reduce circuitry cost, optimise space and minimise power consumption.

Figure 16:
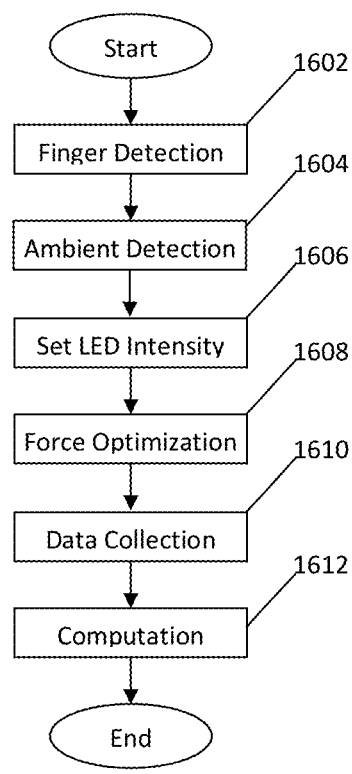
FIG. 16 is a schematic flowchart illustrating an exemplary process for optical monitoring of physiological characteristics of a user in an example embodiment.

FIG. 16 is a schematic flowchart illustrating an exemplary process for optical monitoring of physiological characteristics of a user in an example embodiment. The example embodiment uses an optical measurement device comprising the optional pressure detection assembly (compare 318 of FIG. 3). The illumination and detection assembly of the measurement device comprises a Red LED and an IR LED. The optical measurement device is coupled to a personal mobile processing device.

At step 1602, finger detection is carried out. At step 1604, ambient light detection is carried out. It is appreciated that both the finger detection and ambient light detection can be carried out simultaneously. At step 1606, the light intensity of the LEDs is set. At step 1608, a force optimisation process is carried out whereby, for example, the user is advised to increase/decrease the force exerted on the pressure detection assembly to optimise reading accuracy. At step 1610, data collection is carried out. At step 1612, computation of physiological characteristics of the user is carried out at the personal mobile processing device.

FIG. 17(a) is a schematic flow diagram illustrating a finger detection process in an example embodiment. This process may be carried out in step 1602 of FIG. 16. At step 1702, both the Red and IR LEDs are switched off. At step 1704, it is determined whether the force detected at the pressure detection assembly is more than a pre-stress reading (i.e. without a load) and whether ADC1 of the MCU of the measurement device (compare 418 of FIG. 4) is not saturated. If both the conditions of step 1704 are not met, at step 1706, the personal mobile processing device is configured to alert the user to place the surface portion for measurement, such as a finger, on the measurement device. If both the conditions of step 1704 are met, at step 1708, the finger detection process ends.

FIG. 17(b) is a schematic flow diagram illustrating an ambient light detection process in an example embodiment. This process may be carried out in step 1604 of FIG. 16. At step 1710, both the Red and IR LEDs are switched off. At step 1712, it is determined whether ADC1 of the MCU of the measurement device (compare 418 of FIG. 4) reads a value of e.g. more than about 1.5V. If the reading is more than the exemplary value of 1.5V at step 1712, at step 1714, the personal mobile processing device is configured to alert the user to relocate to another location for the optical measurement as the ambient light interference is determined to be too high. If the reading is less than the exemplary value of 1.5V at step 1712, at step 1716, the ambient light detection process ends.

Figure 18:
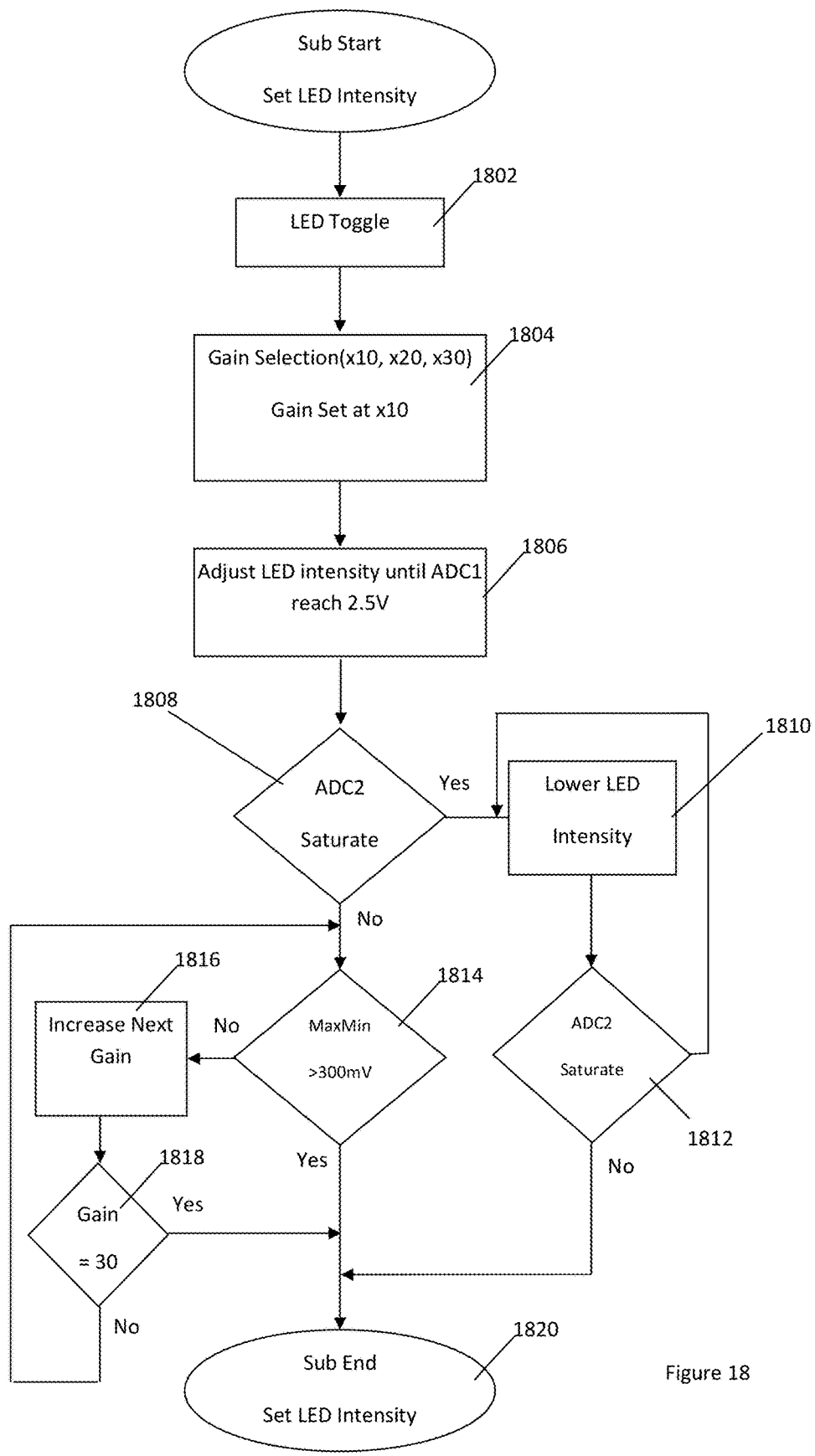
FIG. 18 is a schematic flow diagram illustrating a light intensity setting process in an example embodiment.

FIG. 18 is a schematic flow diagram illustrating a light intensity setting process in an example embodiment. This process may be carried out in step 1606 of FIG. 16. At step 1802, a LED toggle similar to that shown in FIG. 9(b) is performed. At step 1804, the light data detected at step 1802 undergoes a gain process. The gain may be selected from, for example, ten times, twenty times or thirty times etc. In the example embodiment, a gain of ten times is selected. At step 1806, it is determined whether ADC1 of the MCU of the measurement device (compare 418 of FIG. 4) reads a value of e.g. about 2.5V. The LEDs intensity is adjusted until the reading reaches 2.5V. This can ensure that the contribution of the ambient light is not substantially more than the contribution of the LEDs, when measured by the detector. In this example embodiment, because the ambient light cannot exceed 1.5V, and each LED is adjusted to result in a measurement of about 2.5V, the ambient light does not exceed more than about 60% of the light detected by the detector, when each LED is switched on. At step 1808, it is determined whether ADC2 of the MCU of the measurement device reaches saturation, e.g. at about 3.3V. If ADC2 has reached saturation, at step 1810, the LEDs intensity is lowered until ADC2 is no longer saturated at step 1812.

If ADC2 has not reached saturation at step 1808, at step 1814, it is determined whether the maximum and minimum data points have a difference of more than e.g. about 300 mV. If the difference at step 1814 is not more than e.g. about 300 mV, at step 1816, the gain can be increased. At step 1818, it is determined whether the gain is thirty times. If the gain is thirty times, the LED intensity is set and the setting process is ended at step 1820. If the gain is not yet thirty times at step 1818, the process loops back to step 1814.

Figure 19:
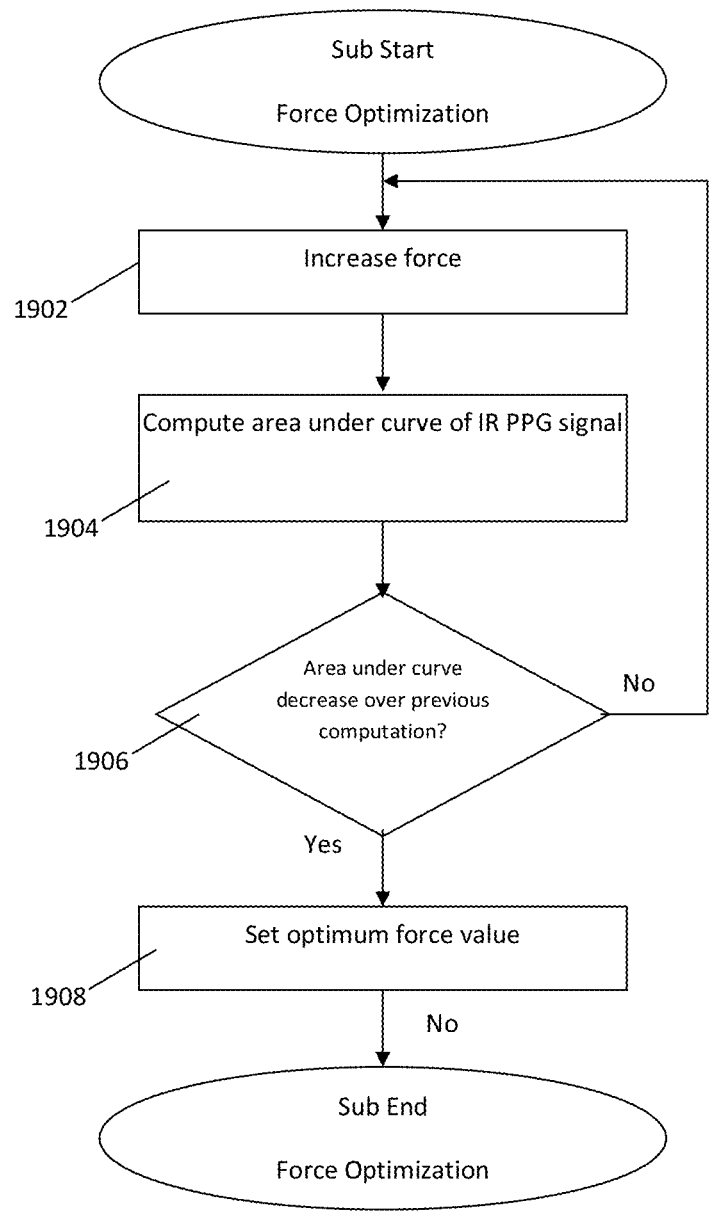
FIG. 19 is a schematic flow diagram illustrating a force optimisation process in an example embodiment.

FIG. 19 is a schematic flow diagram illustrating a force optimisation process in an example embodiment. This process may be carried out in step 1608 of FIG. 16. Reference is also made to the description of FIGS. 27, 28(a) to (c). A graphical user interface (GUI) is shown on a personal mobile processing device to a user. At step 1902, a force bar is provided on the GUI. The user is informed to increase pressure on the measurement surface of the optical device to increase the force bar. At step 1904, an area under the curve for the obtained PPG signal is computed for the particular force value. At step 1906, it is determined whether the area computed at step 1904 has decreased as compared to a previous computation. This is to determine a highest amplitude of a PPG signal. If the highest amplitude is not obtained, the process loops back to step 1902 to inform the user to exert a larger pressure on the optical measurement device. If the highest amplitude is obtained, at step 1908, the optimum force value is obtained.

Figure 20:
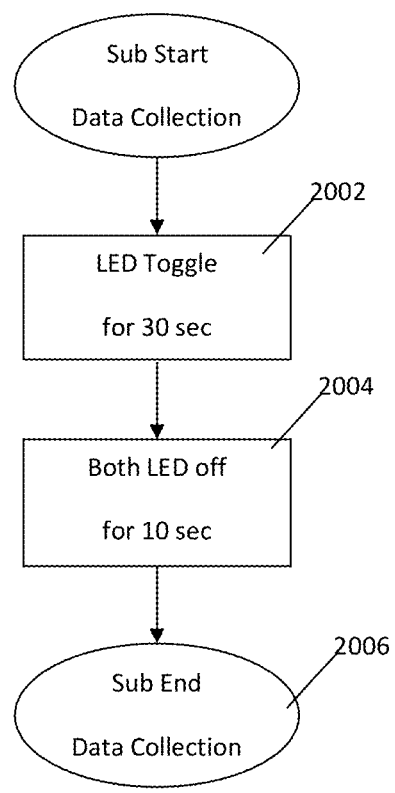
FIG. 20 is a schematic flow diagram illustrating a data collection process in an example embodiment.

FIG. 20 is a schematic flow diagram illustrating a data collection process in an example embodiment. This process may be carried out in step 1610 of FIG. 16. At step 2002, a LED toggle similar to that shown at numeral 806 of FIG. 8 is performed for about 30 seconds. PPG signal data is collected from the toggling sequence. At step 2004, the Red and IR LEDs are switched off for ambient PPG signal data to be collected for about 10 seconds. Compare 802 of FIG. 8. In this example embodiment, the ambient PPG signals are collected over a shorter period than the time taken for the LED IR and Red PPG signals. At step 2006, the data collection process is ended.

Figure 35:
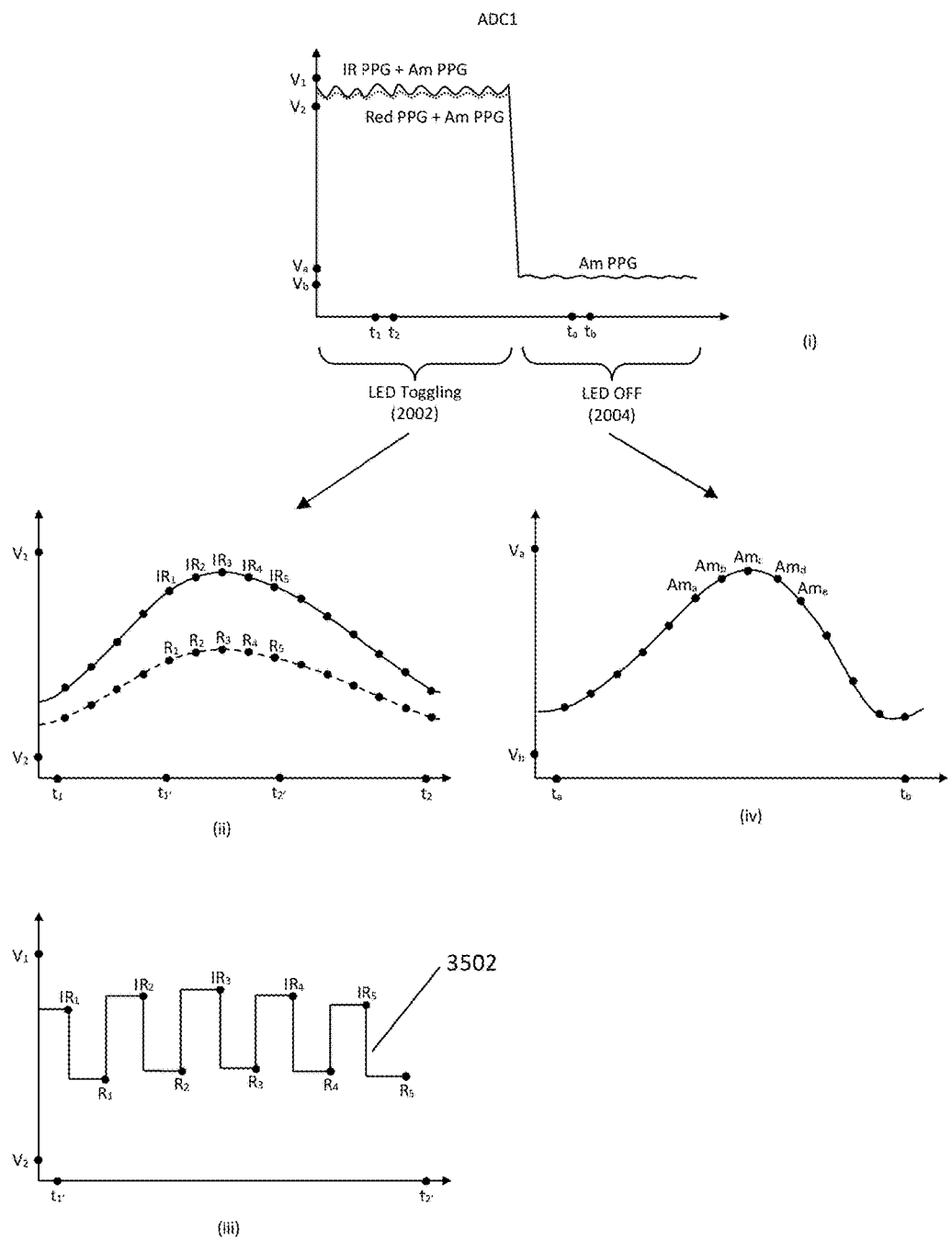
FIG. 35 shows how a signal forms at an analog to digital converter when two LEDs toggle and when both LEDs are switched off in an example embodiment.

FIG. 35 shows how a signal forms at an analog to digital converter (compare ADC1 422 of FIG. 4) when two LEDs toggle and when both LEDs are switched off in an example embodiment. During toggling, the signal detected at a photodetector PD is shown in part (iii) of FIG. 35. The square wave 3502 is the detected signal which reflects the sampled points based on the toggling timing sequence. At each sampled point of Red ($R_1, R_2 \ldots R_n$,) and IR ($IR_1, IR_2, \ldots IR_n$), analog to digital conversion ADC is executed and the values captured by a microcontroller MCU. Data is separated or de-multiplexed in the MCU and can be processed as separated Red and IR PPG signals, as shown in part (ii) of FIG. 35. Over a larger time frame, a PPG signal comprising Red and IR are formed, as shown in part (i) of FIG. 35. When both LEDs are switched off, only 1 signal (Ambient) is present and thus the ADC captured values are not separated. This signal at part (i) passes through the signal conditioning and produces a signal substantially similar to FIG. 10(*b*).

Figure 21:
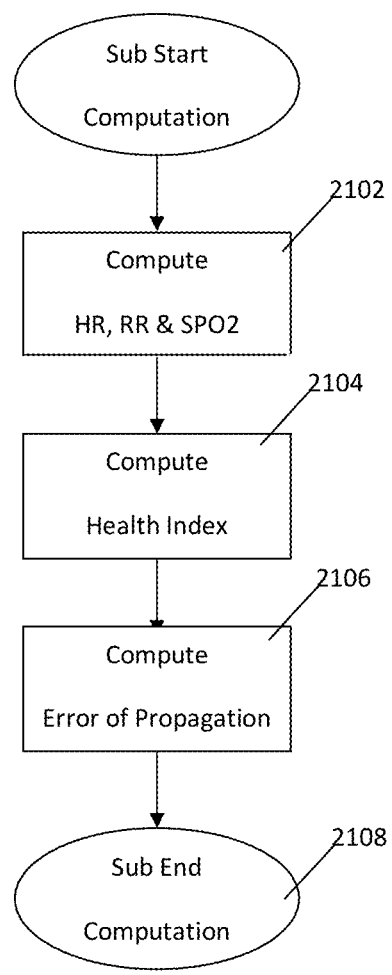
FIG. 21 is a schematic flow diagram illustrating computation of physiological characteristics of a user in an example embodiment.

FIG. 21 is a schematic flow diagram illustrating computation of physiological characteristics of a user in an example embodiment. This process may be carried out in step 1612 of FIG. 16. The computation is carried out at a personal mobile processing device. At step 2102, physiological characteristics such as heart rate, respiratory rate and SpO2 of the user can be computed. At step 2104, a health index may be computed based on the computation at step 2102. This may be a chart showing the user a health status. At step 2106, an error of propagation may be computed. This may be shown as an illustration to the user to inform the user on the accuracy of the computations. At step 2108, the computation of physiological characteristics is ended.

In example embodiments wherein the optical measurement device comprises the optional pressure assembly, a personal mobile processing device coupled in cableless configuration to the optical measurement device can be configured to detect and display an amount of pressure applied by a body part of a user to the device during the optical measurement. When the user applies an appropriate amount of pressure to the optical measurement device, the resulting signal-to-noise ratio of the detected optical measurement signal can be increased, and a more accurate measurement signal can be obtained from the user. An optimal pressure can be determined in real-time at the personal mobile processing device by analyzing the detected optical measurement signal from the optical measurement device and correlating a high signal-to-noise ratio portion of the signal with a corresponding applied pressure. The user can then be provided real-time feedback by the personal mobile processing device indicating whether the amount of pressure being applied by the user should be increased, decreased or maintained at the same level. Thus, the personal mobile processing device coupled to the optical measurement device can therefore provide an optimum pressure determination customized for each individual user, thereby obtaining a resulting optimum measurement signal for each user.

As described, the acquisition of a physiological signal representing a change in the volume of an organ in the body through the use of optical measurement is known as a photoplethysmograph (PPG). Obtaining optical PPG signals may be related to application of external pressure on the body surface which is being measured. The pressure is related to obtaining a good quality PPG signal with a high signal to noise ratio.

Figure 22:
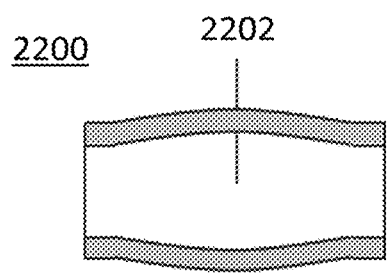
FIG. 22 is an illustration of a cross-section of a blood vessel when a low external pressure is applied.
Figure 23:
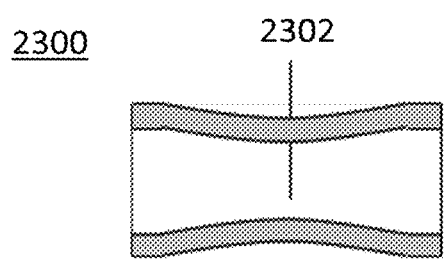
FIG. 23 is an illustration of the cross-section of the blood vessel when a high external pressure is applied.
Figure 24:
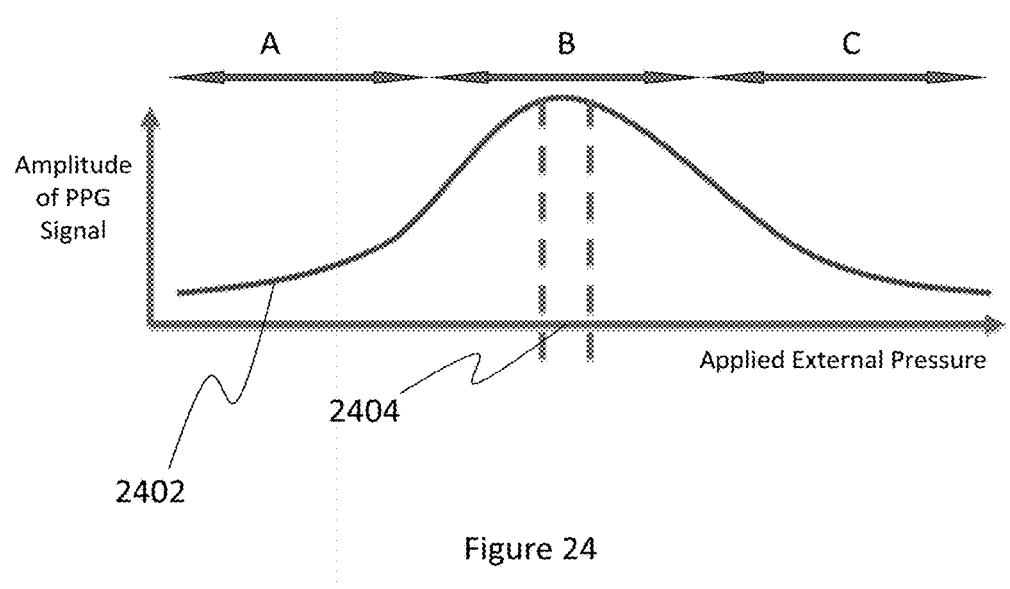
FIG. 24 is a graphical illustration of the amplitude of a measured PPG signal in comparison with an amount of applied external pressure in a state of zero transmural pressure.

However, the externally-applied pressure cannot be too large or too small, or the quality of the detected PPG signal will be low. For example, as illustrated in a cross section of a blood vessel 2200 in FIG. 22, in the event of an insufficient exertion of external force as compared to internal arterial pressure at a measurement site 2202, the internal pressure is too low to obtain a proper measurement, and low PPG signals are obtained. On the contrary, as illustrated in FIG. 23, the application of too much external force causes the blood vessel 2300 to be occluded at the measurement site 2302 where the pressure is applied, resulting in resistance of regular blood flow and generating skewed PPG signal data. If the external pressure is too small or too high, the reaction pressure at the wall of the blood vessel 2200,2300 is low, and thus a small PPG signal will be observed. FIG. 24 is a graphical illustration of the amplitude 2402 of a measured PPG signal in comparison with an amount of applied external pressure. With a low applied pressure in range A, the amplitude 2402 is correspondingly low. As the applied pressure is increased, in range B, the amplitude also increases. However, when the applied pressure increases beyond a certain point, the amplitude decreases again, as shown in range C.

To obtain a strong PPG signal, the external pressure should be sufficient to minimize transmural pressure such that the external pressure is equal to the internal pressure. Further illustrated in FIG. 24 is a range 2404 within range B where the amplitude of the PPG signal is at its peak. Within this range 2404, an externally-applied pressure is instantaneously balanced with the internal arterial pressure, thus resulting in a state of zero transmural pressure. At zero transmural pressure, the arterial walls are unloaded and the arteries will not change in size. Consequently, the blood volume within the arteries at the measured region will not change and can be accurately measured to provide a good quality PPG signal.

In an exemplary embodiment, the pressure assembly seeks to achieve and to maintain an optimal pressure for obtaining an optimum PPG signal over an extended period of time. By providing real-time, instantaneous feedback via a personal mobile processing device to a user being measured, the user is able to instantly adjust the amount of pressure being applied to the optical measurement device in order to obtain an optimum PPG signal. However, the optimum pressure may not only be a result of a state of zero transmural pressure, but may also result from the effects of absorption and scattering paths of light as light travels in and out of a portion of tissue of a user being measured. For example, where the pressure is too low, a light source may not be able to penetrate the tissue surrounding the blood vessel which is being measured. Therefore, light may not travel in and out of the finger effectively enough for a good PPG signal to be detected. Where the pressure is too high, light may be absorbed or scattered such that the amount of light detected is insufficient to obtain a good PPG signal.

In one exemplary embodiment, the personal mobile processing device may provide feedback to the user indicating whether the user is applying insufficient pressure, too much pressure or the correct amount of pressure. The feedback to the user may be visual or auditory in the form of a visual display or audible sounds, and may particularly be a display of the real-time PPG signal being captured by the device. The feedback may also be a more simplified display indicating whether the user should take action to increase or reduce the amount of pressure being applied to the device. In another embodiment, the feedback may be in the form of tactile feedback, wherein the optical measurement device produces e.g. a small vibration when the applied pressure is at an optimum range.

Exemplary embodiments described herein may provide a device and method capable of augmenting signal to noise ratio in an optical signal of an illuminated region at a measuring site of a body part of a user. Exemplary embodiments also provide for detecting the optical response formed by both light reflected from the measuring site and the light transmitted through the measuring site. Exemplary embodiments described herein utilize redirecting reflections of light on its way towards the measuring site (i.e. blood vessels) back to the region of interest.

In an additional exemplary embodiment, the device may perform a series of calibration steps for each individual user in order to determine an optimum range of pressure for each individual. The subsequent steps of capturing the PPG signal will then use the predetermined optimum range as the benchmark for obtaining an optimum PPG signal.

The integration of the pressure detection assembly with the illumination and detection assembly can provide a simple, comfortable interaction for the user, and the use of a pressure detection assembly which provides real-time feedback via a personal mobile processing device to the user improves the quality, or amplitude, of the received PPG signals. The optical measurement device is connected with a personal mobile processing device/feedback unit which receives the PPG signals and pressure measurements from the optical measurement device and provides feedback to the user regarding the amount of pressure being applied.

The illumination and detection assembly may be referred to as a PPG sensor, and includes a light source and a plurality of light detectors, where the light source propagates light through a portion of living tissue at a measurement site of a user. The light detectors then detect light which is transmitted through the portion of living tissue of the user or which is reflected from the portion of living tissue of the user.

In one exemplary embodiment, the pressure detection assembly is a pressure sensor that detects the amount of pressure that has been applied by a body part of the user, such as a finger. The pressure sensor may be a thin film flexible printed circuit, such as a piezo-based or piezoresistive sensing device whereby a resistance change sensed by the circuitry is inversely proportional to a change in force applied on the sensing device. In some example embodiments, the circuit is a micro-electro-mechanical (MEMS) strip. Nevertheless, any other force measuring device that is capable of sensing an applied contact force may be used.

Figure 33:
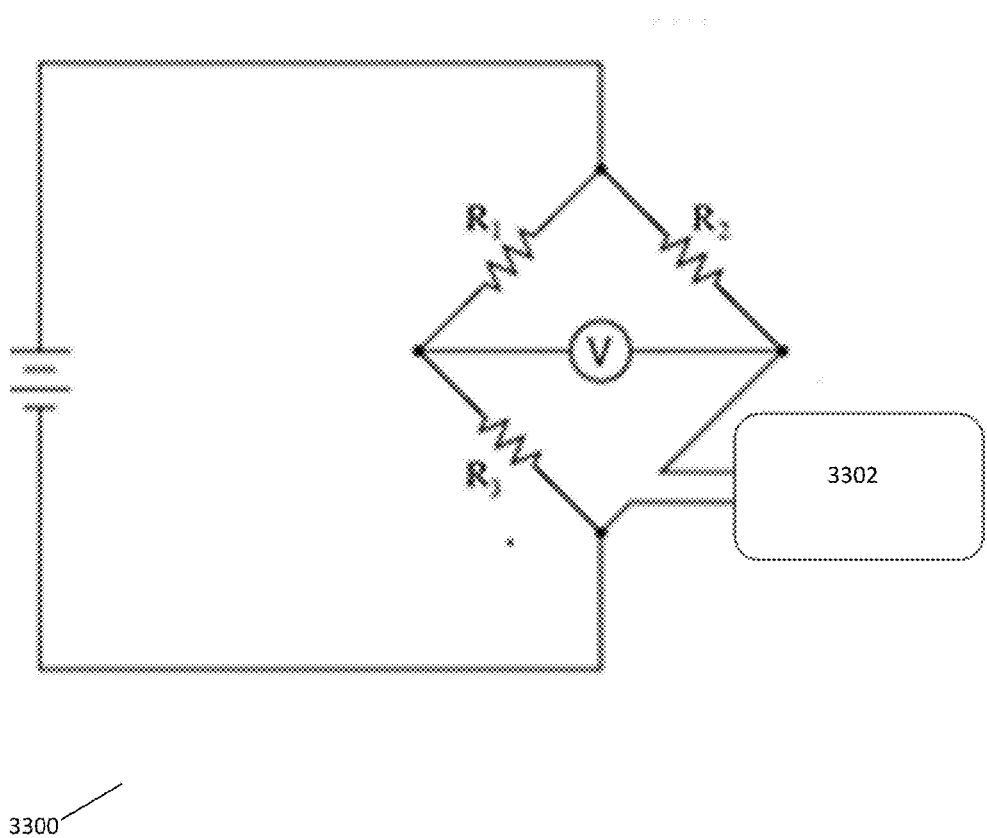
FIG. 33 shows a simplified exemplary representative circuit diagram for implementing a piezo-based sensing device in an example embodiment

FIG. 33 shows a simplified exemplary representative circuit diagram for implementing a piezo-based sensing device 3300 disclosed herein, in an example embodiment. V represents a voltmeter, and R1, R2 and R3 represent a plurality of electrical resistors. Component 3302 represents a piezo-based material (e.g. piezoelectric or piezoresistive) which can be depicted as one or more electric resistors, one or more of which being variable resistors with resistance being dependent on the force applied thereto. It will be appreciated by a skilled person that the position of Component 3302 can be interchanged with any one of R1, R2 and R3 or vice versa if desired. R1, R2, R3 and Component 3302 are connected in a Wheatstone bridge configuration. The bridge configuration shown in FIG. 33 is in a quarter-bridge configuration. Nevertheless, if desired, the bridge can also be operated in a half or full form, that is, with one or more components similar to Component 3302 replacing R2 or R1, R2 and R3 respectively. One or more fixed or variable electrical resistors can also be added as "dummy" force gauges to complete the bridge circuit as and when desired, for example to negate the effects of temperature changes.

In one example working implementation when the bridge is operated in a quarter configuration shown in FIG. 33, R2 is set to a value equal to the resistance of Component 3302 with no force applied. The other two resistors R1 and R2 are set to be equal to each other. In such an arrangement, when no force applied to Component 3302, the bridge is symmetrically balanced, that is, the voltmeter V indicates zero volts, representing zero force on the component 3302. When force is being applied to Component 3302, its resistance varies, i.e. decreases or increases, respectively, thus unbalancing the bridge and producing a non-zero reading on the voltmeter V. The readings obtained on the voltmeter can then be correlated to the actual mechanical force applied on component 3302.

The pressure detection assembly may comprise a microelectromechanical system (MEMs). In one embodiment, the pressure detection assembly comprises a piezo-based sensor which measures the force applied to a material by correlating based on physical an/or electrical property changes of the material due to mechanical stress. Such material can include but is not limited to crystals, ceramics or semiconductors. The electrical property changes can include but are not limited to changes in conductivity, resistivity, resistance, capacitance and/or generated electric charge of the material, The piezo-based sensor can be selected from a group consisting of a piezoelectric based sensor, a piezoresistive based sensor, a piezocapacitive based sensor or the like. In exemplary embodiments, a force transmitting member is rested on the pressure sensor and transmits the force applied thereto to the pressure sensor without substantial displacement or deformation of the force transmitting member. In such embodiments, while some displacement or deformation may be present (for e.g. in a microscale), these displacements or deformations may not be appreciable to the naked human eye.

Advantageously, the pressure sensor can be easily installed in the optical measurement device without adversely compromising on the overall compactness. In such embodiments, little or substantially no displacement or deformation may be required to produce an accurate reading of the applied force. This again beneficially reduces the amount of space within the measurement device required for allowing any displacement or deformation to take place. Even more advantageously, as the moving parts involved are reduced, there may be less wear and tear of the internal components, thereby increasing the life span of the device.

Figure 25A:
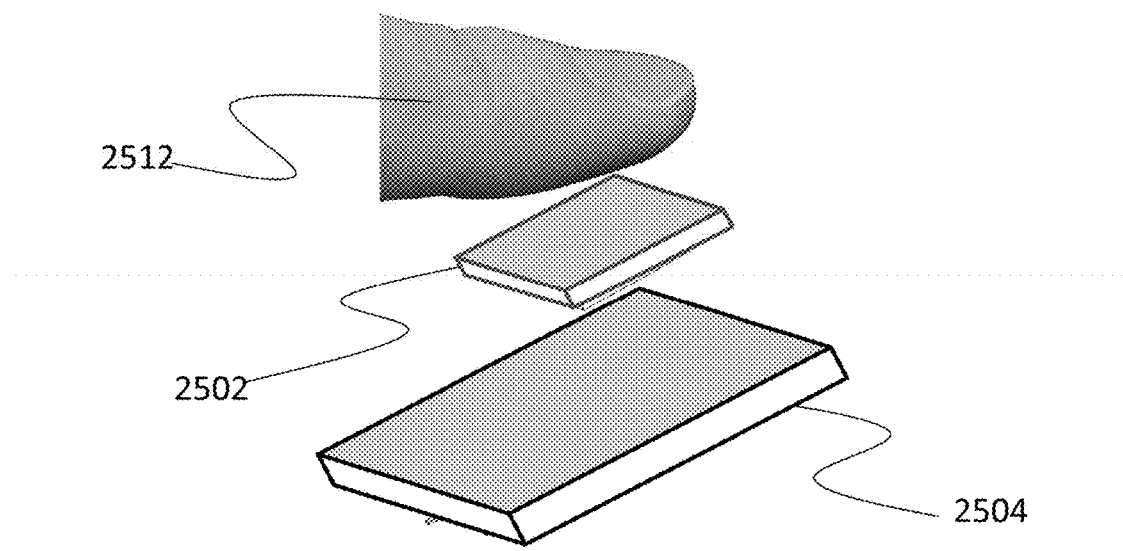
FIGS. 25(a) and (b) are schematic expanded view illustrations of an optical measurement device in an example embodiment.
Figure 25B:
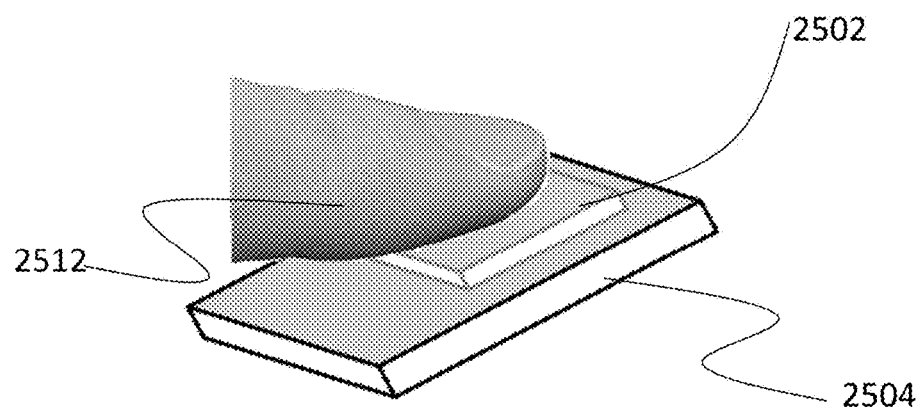

As illustrated in the exploded view of an optical measurement device in FIG. 25(a), the pressure sensor 2504 may be positioned below the PPG sensor 2502, so that the force applied by a user's finger 2512 is translated through the PPG sensor 2502 to the pressure sensor 2504. The pressure sensor 2504 then gathers and tracks the external force exerted by the user's finger 2512. FIG. 25(*b*) illustrates an assembled view of the pressure sensor 2504 together with the PPG sensor 2502 in operation, where the user's finger 2512 is placed in contact with the PPG sensor 2502.

The feedback unit (compare 414 of FIG. 4) may be in the form of a computer including a processor, a memory and optionally a display, as is further described below with regard to FIG. 26. The feedback unit receives a PPG signal and pressure measurements from the optical measurement device, and temporally correlates the PPG signal with the pressure measurements in order to determine an optimal amount of pressure that provides an optimal PPG signal, as shown in the comparison PPG signal graph 2702 and applied pressure graph 2704, illustrated in FIG. 27 and described in more detail below.

In an example embodiment, the feedback unit 2806 may be provided with a display 2814, as illustrated in FIGS. 28(*a*) and (*b*). The display 2814 may provide visual feedback to the user in the form of a graphical user interface (GUI) during the process of measuring the PPG signal. The visual feedback may be a real-time display of the detected PPG signal 2816 so that the user can instantly see the effect of varying the amount of pressure being applied to the optical measurement device 2800 and adjust the amount of pressure until an optimum PPG signal is displayed. The display 2814 may also provide a real-time graphical indication 2818 of the pressure being applied. The graphical display 2818 of the applied pressure may track the PPG signal 2816 on the same graphical display (compare e.g. FIG. 29(*a*), below), or perhaps be displayed in the form of a vertical pressure status bar 2820 positioned on one side of the displayed PPG signal, as illustrated in FIGS. 28(*a*) and (*b*). The status bar 2820 can move up and down depending on the amount of force being applied by the user. In this embodiment, the user identifies an optimal PPG signal in order to determine whether the displayed real-time PPG signal 2816 can be improved. However, by displaying the detected PPG signal 2816 and possibly the pressure status bar 2820, the feedback unit 2806 is not required to compute an amount of pressure that provides an optimum PPG signal, as the user is performing this step manually by analyzing the displayed PPG signal 2816 and making adjustments without guidance by the device. FIG. 28(*b*) illustrates the feedback unit 2806 and the optical measurement device 2800 in operation, where a user's finger 2812 is positioned on the optical measurement device 2800.

In an exemplary embodiment illustrated in FIG. 28(*c*), the feedback unit 2806 may generate and display a GUI with a more simplified indication of whether the user should adjust the amount of pressure to provide more, less or the same amount. There may be any number of ways to provide this type of GUI. For example, symbols or shapes—perhaps even color-coded in a traffic-light colored display—may be displayed to tell the user to adjust the amount of force being applied. Similarly, the GUI may simply display words telling the user to "Apply More Pressure, "Apply Less Pressure," or "Apply the Same Amount of Pressure." In FIG. 28(*c*), a highlighted box 2822 may be placed over the pressure status bar 2820 to identify an optimum range at which pressure should be applied for a particular user. In this embodiment, the feedback unit 2806 analyzes and compares the measured PPG signal and corresponding applied pressures in real-time in order to determine a range of applied pressure which provides the highest amplitude of PPG signal—usually a state of zero transmural pressure. The feedback unit 2806 can then provide corresponding indicators to the user on the display depending on whether the user is applying pressure within, above or below the determined range.

In an exemplary embodiment, the feedback unit may not require a display, as it could provide audible commands to the user through a speaker or other audio output component. For example, the audio device could simply talk to the user to say "Apply More Pressure," "Apply Less Pressure," or "Apply the Same Amount of Pressure." The audio feedback could also be in the form of musical tones of different pitches or sounds—such as a ringing sound or buzzer sound—which are widely known as positive or negative sounds.

In another exemplary embodiment, the optical measurement device may assist in allowing the user to calibrate the device before actual measurement of the PPG signal is carried out. This may involve the feedback unit asking the user to apply a variety of different pressures to the optical measurement device during a fixed period of time, during which the feedback unit measures the PPG signal detected during that time period and determines a range of applied pressure which obtains an optimal PPG signal. For example, the user may be asked to exert pressure while following a profile of pressure ranges over a period of time, such as the force profile 2708 in the applied pressure graph 2704 in FIG. 27. As a result of the calibration, the personal mobile processing device/feedback unit is able to obtain a range of applied pressure for each individual user, rather than a generalized range which may not be accurate depending on the individual user being measured.

In one exemplary embodiment, the feedback unit may be a portable device, such as a mobile phone, smartphone, personal digital assistant (PDA), tablet, netbook or laptop, although this list is not exhaustive by any means. However, the feedback unit may not need to be portable, and could similarly be a computer or server. The feedback unit may be connected with the optical detection device in a wired or wireless fashion, or through a proprietary connector, such a universal serial bus (USB) port or the 30 pin connection used in the Apple® iPhone® (Apple Computer, Inc., Cupertino, Calif.).

Figure 30A:
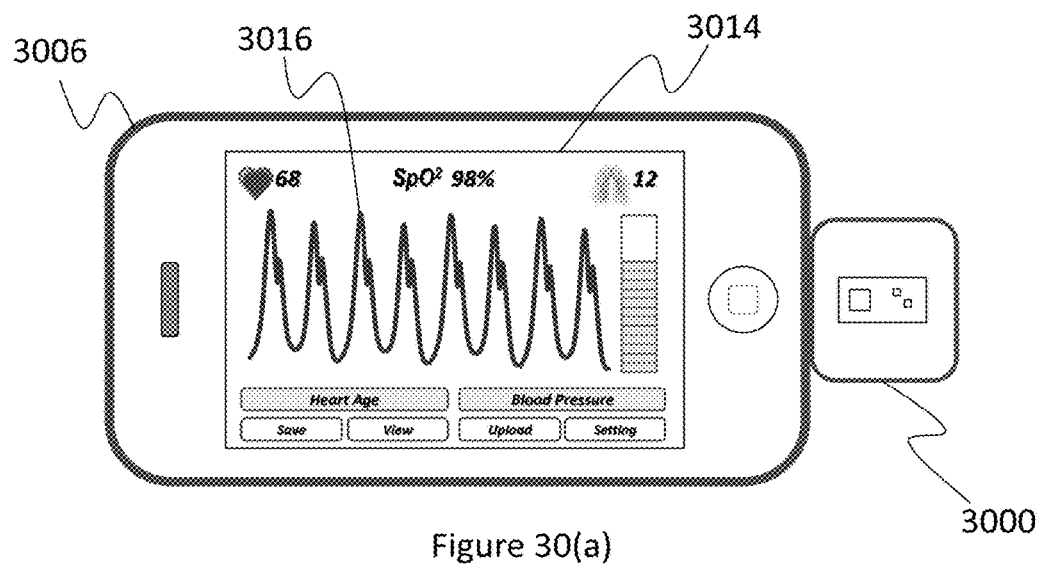
FIGS. 30(a) and (b) schematically illustrate a feedback unit/personal mobile processing device coupled to an optical measurement device configured in a landscape orientation in an example embodiment.
Figure 30B:
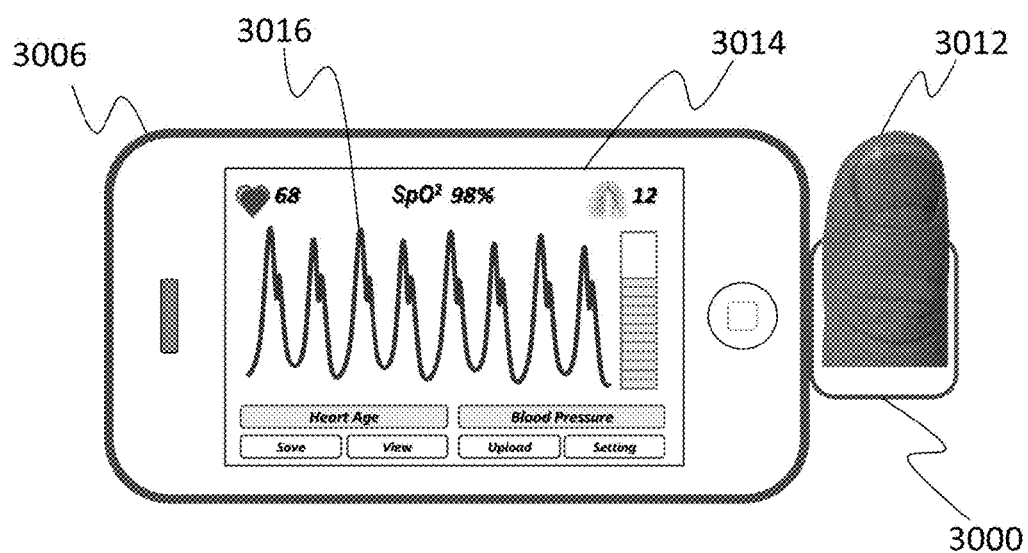

FIGS. 30(*a*) and (*b*) illustrate yet another exemplary embodiment, where the portable device 3006 may be oriented in a landscape configuration such that the user views the display 3014 horizontally and interacts with the optical detection device 3000 in a way that is easier for the user to hold the portable device 3006 in the user's hands. In landscape orientation, the user can place a finger 3012 on the optical detection device 3000 and more easily view a larger time period of the PPG signal 3016.

The feedback unit may also include software or other computer programmable instructions which carry out instructions relating to receiving and processing the PPG signal, the pressure measurements, and creation of the output to the user relating to the correlation of the detected PPG signal and pressure measurements.

The monitoring of (i) the PPG signal from the illumination and detection assembly and (ii) the amount of force exerted by an individual from the pressure assembly thus enables the optical measurement device to obtain an optimum PPG signal with a high signal to noise ratio. The signal to noise ratio is augmented in an optical signal. The optical measurement device provides for a PPG signal to be acquired at a zero transmural pressure that is unique to each user using the device.

The resulting optimal PPG signal provides a highly accurate measurement of various physiological parameters detected by photoplethysmography, such as a saturation level of oxygen in blood.

Figure 27:
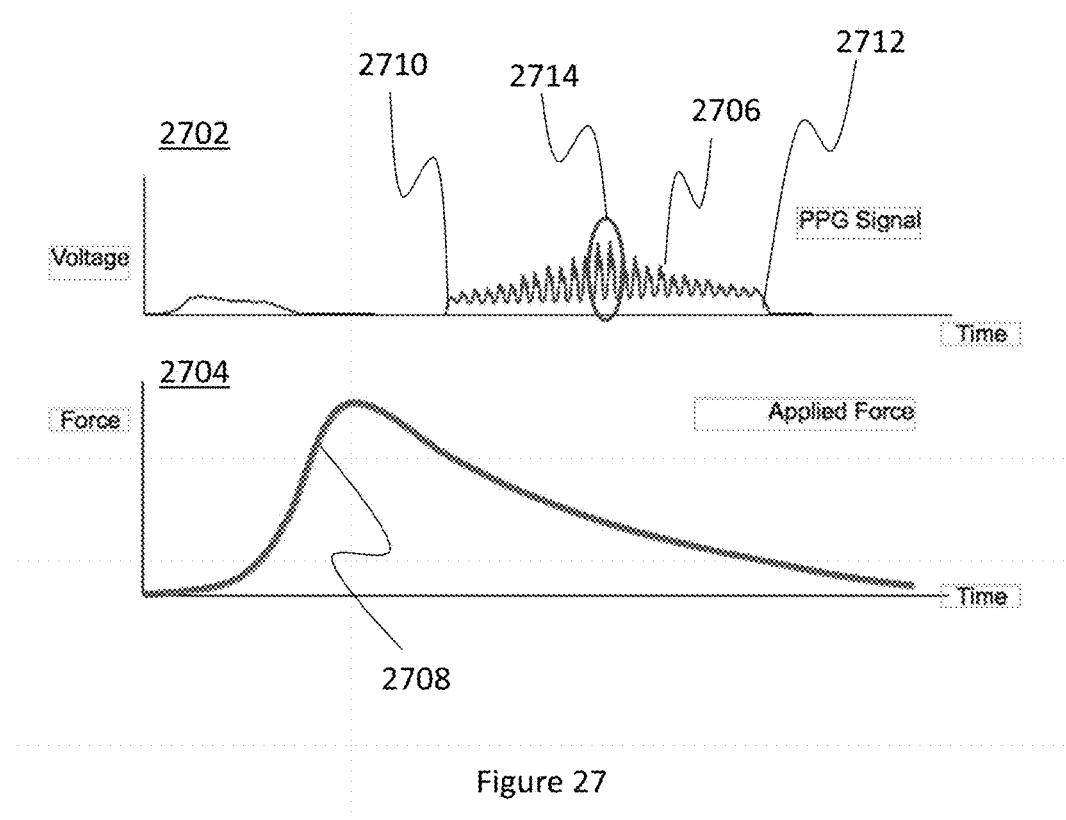
FIG. 27 schematically illustrates a graphical comparison of a graph of measured voltage of a PPG signal over time in correspondence to a graph of an applied amount of pressure over time in an example embodiment.
Figures 28A, 28B:
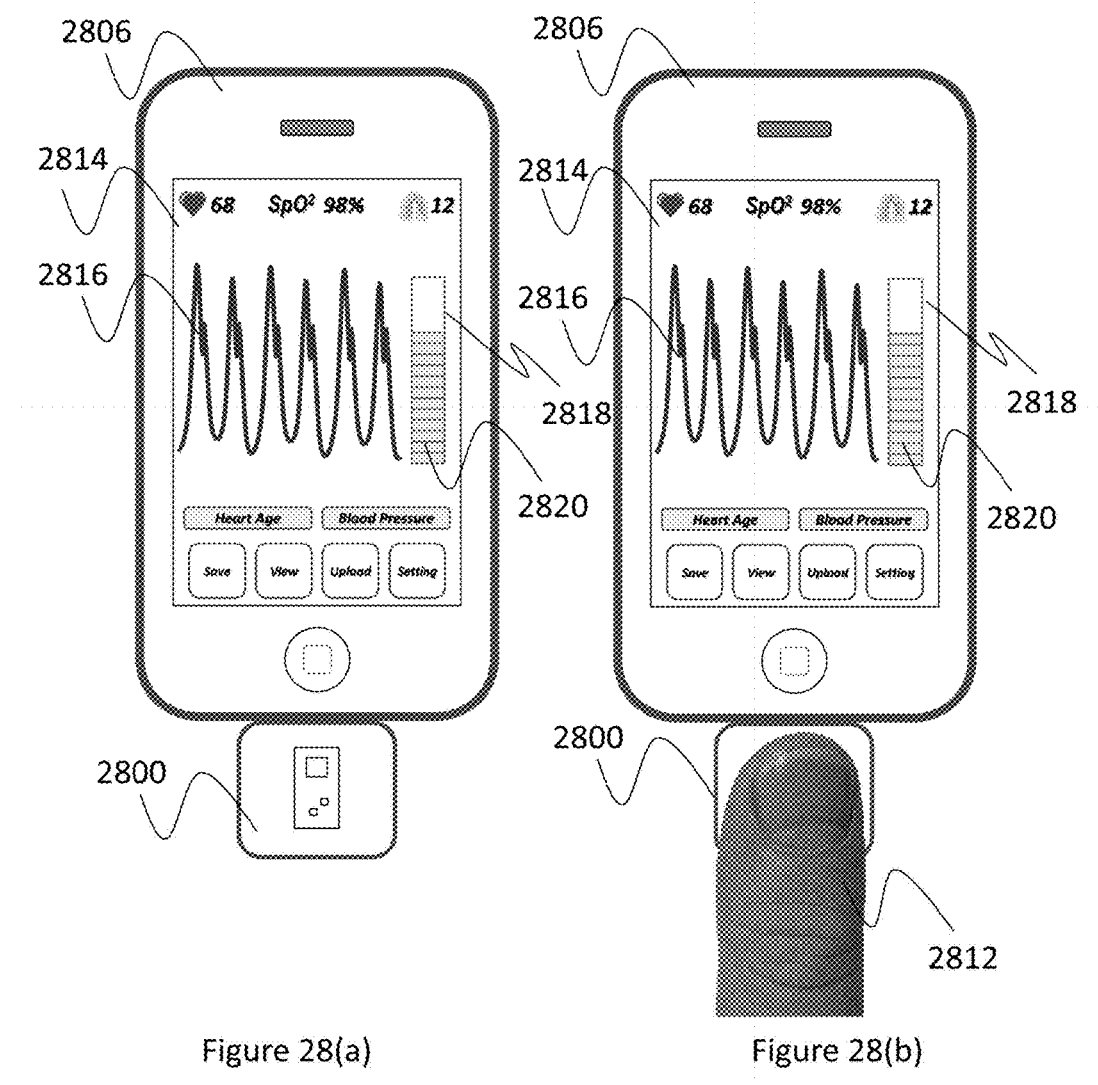
FIGS. 28(a) and (b) schematically illustrate a graphical user interface (GUI) of a feedback unit in coupling relationship to an optical measurement device in an example embodiment.
Figure 28C:
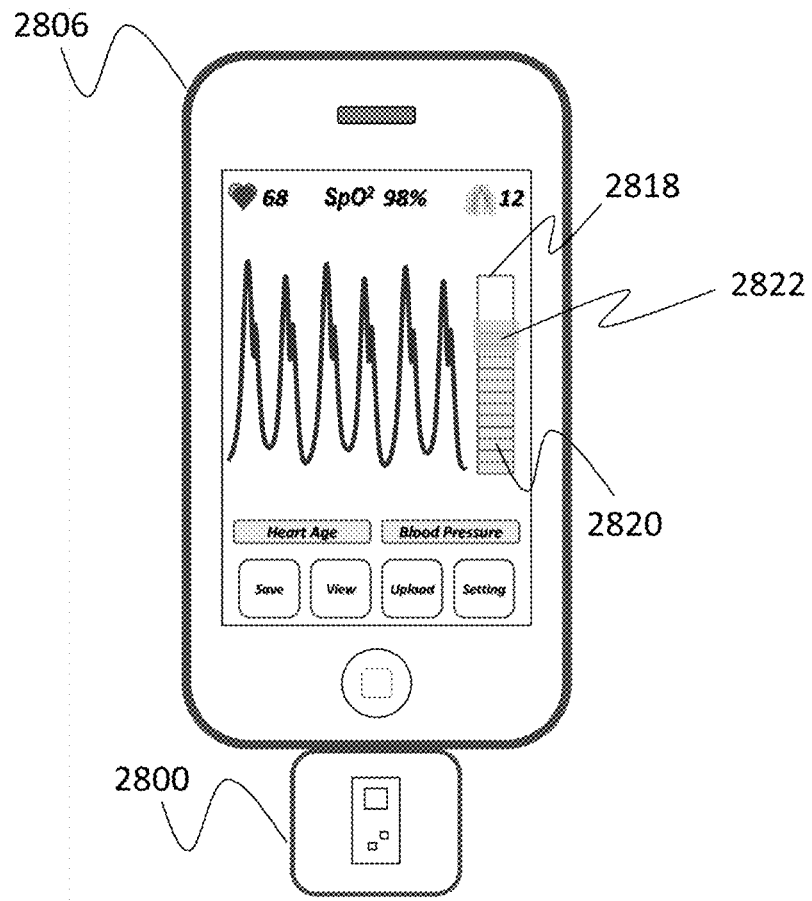
FIG. 28(c) schematically illustrates a graphical user interface (GUI) of a feedback unit for indicating whether a user should adjust the amount of pressure to provide more, less or the same amount in an example embodiment.
Figure 31A:
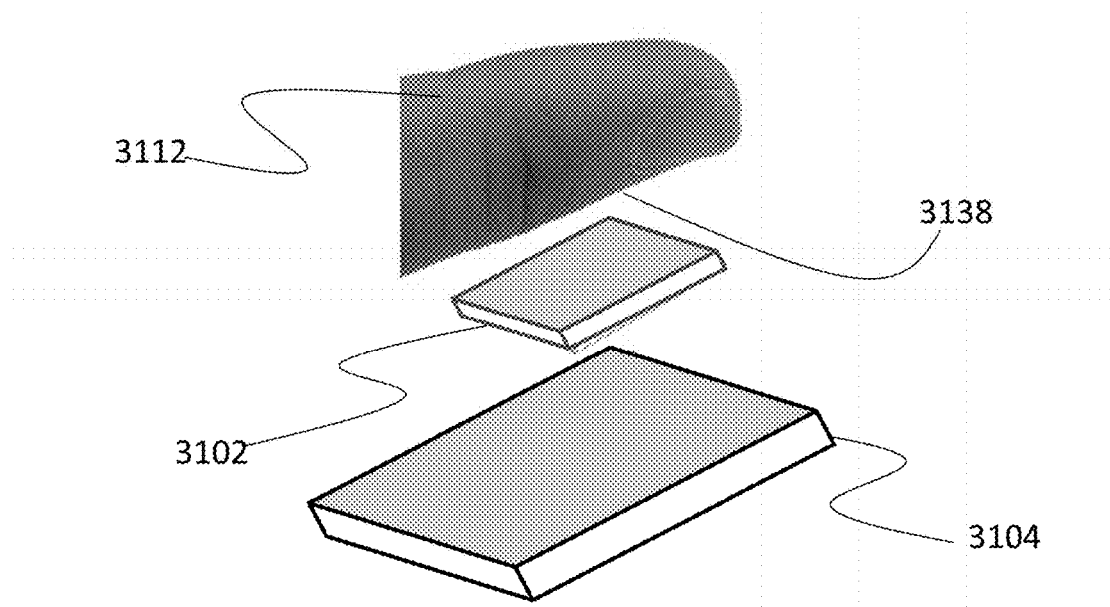
FIGS. 31(a) and (b) are schematic expanded view illustrations of using an optical measurement device to interact with a surface portion of a user for measurement in an example embodiment.
Figure 31B:
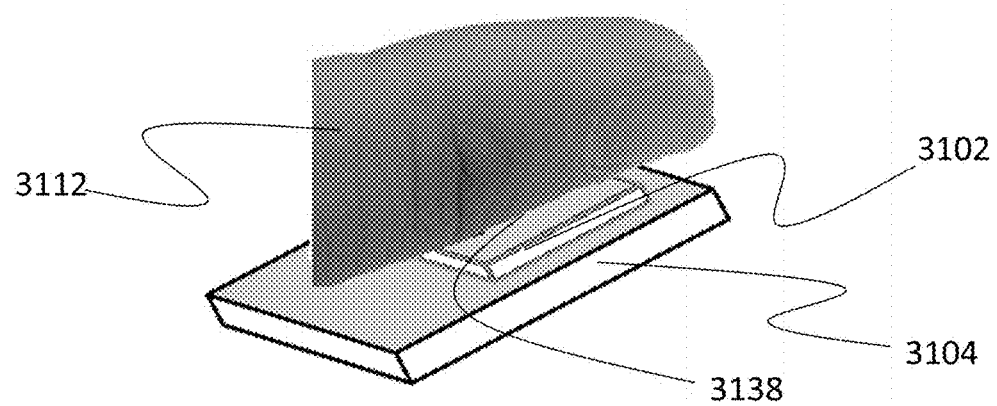

In another embodiment, the optical measurement device further includes acquisition of systolic and diastolic blood pressure parameters. One option for detecting the parameters to determine blood pressure involves placing the side 3138 of the finger 3112 where the digital artery lies onto the illumination and detection assembly 3102, as illustrated in FIGS. 31(*a*) and (*b*). As shown in FIG. 27, a PPG signal 2706 in the PPG signal graph 2702 is monitored while the user applies vertical downward force onto the pressure sensor 3104 following a pre-determined applied force profile 2708 with respect to time, as shown in the applied pressure graph 2704. The basic fundamental behind this analysis is to identify when the PPG signal 2706 begins to display a PPG waveform (point 2710) and when the PPG signal finally dies off (point 2712), as these points are indirectly associated with the highest and lowest point of the blood pressure. In addition, with this analysis, the external pressure needed to achieve zero transmural pressure can be determined. When zero transmural pressure is achieved, the PPG waveform reflects the highest amplitude, as shown at area 2714 in the PPG signal graph 2702. In FIG. 27, as the amount of applied pressure follows the profile 2708 of rapid increase and gradual decrease over time, the PPG waveform 2706 changes in amplitude accordingly. Thus, looking at the entire range of PPG waveform from 2710 to 2712 with respect to applied force 2708, the highest amplitude PPG waveform 2714 provides an indication of the corresponding position on the applied pressure graph 2704 where an amount of applied pressure results in zero transmural pressure state.

Figure 32:
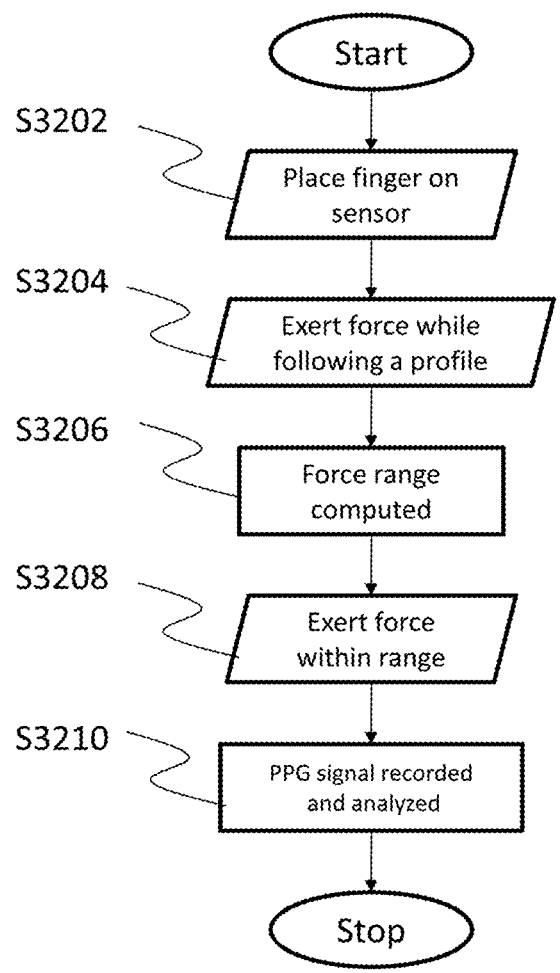
FIG. 32 is a schematic flow chart illustrating a method of measuring a PPG signal on an optical measurement device coupled to a feedback unit and using feedback from a pressure detection assembly in an example embodiment.

One exemplary embodiment of a method of using the optical measurement device comprising a pressure assembly and coupled to a feedback unit is described herein with reference to FIG. 32, with a corresponding exemplary GUI illustrated in FIGS. 29(*a*) to (*c*).

A user seeking to obtain his or her PPG signals can first place a body part, such as a finger, on the measurement/sensor surface of the optical measurement device (S3202). Calibration of the device to the individual user may be performed (S3204), where the user is asked to apply an amount of pressure over a specific period of time, corresponding to a force profile 2704 (see FIG. 27). In other words, the user is asked to vary the applied pressure such that the system can determine an optimum pressure for the user by analyzing the resulting PPG waveforms that result from the variety of applied pressures (S3206). The user may also be presented with at least one measured PPG waveform generated by a particular amount of applied pressure, as illustrated in the graphical displays in FIGS. 29(*b*) and (*c*).

FIG. 29(*a*) is a graphical display 2906 which shows the relationship of a calculated area 2910 under the curve in FIGS. 29(*b*) and (*c*) with respect to applied pressure 2908. FIGS. 29(*b*) and (*c*) are graphical displays 2902 and 2904, respectively, which illustrate the different PPG waveforms at different applied pressures, and how the area under curve of the PPG waveform is computed.

As shown in FIG. 29(*a*), the optimum pressure 2918 applied in FIG. 29(*c*), about 299 mmHg, corresponds to the largest area 2910 of PPG waveform detected during the calibration (S3204). Once this optimum pressure is determined, a subsequent measurement period begins, during which the user is asked, via the feedback unit, to apply pressure within an optimum range above and below the optimum pressure (S3208). As previously described with regard to FIG. 28(*a*), the amount of pressure being applied by the user may be displayed in a graph 2818 on the display 2814 so that the user can see the amount of pressure being applied in real-time. The graph 2818 may also be displayed using the pressure status bar 2820. If the amount of force being applied by the user falls outside of the optimum range, the system can detect this in real-time and can ask the user to increase or decrease the applied pressure in order to remain within the range of optimum pressure and record the best possible PPG signal quality (S3210).

Optimum pressure is determined as the pressure at which the measured PPG signal has the largest waveform amplitude, or area 2912 under the PPG waveform, as shown in FIG. 29(*b*) by the area 2912 bounded by the PPG signal 2914 and baseline 2916. FIG. 29(*a*) then graphs the variation of the area 2912 under the PPG waveform with respect to the pressure 2908 applied on the sensor/measurement surface. As may be observed in this example, the optimum pressure 2918 is at about 299 mmHg, where area 2912 under the curve is at its maximum of about 11.63.

Thus, the above described example embodiment can provide an optical measurement device for obtaining non-invasive physiological measurements from a portion of living tissue and method of using the same, which more particularly comprises a pressure detection assembly configured to detect and display, via a feedback unit, an amount of pressure applied by a body part of a user to the optical measurement device during the optical measurement. When a user applies an appropriate amount of pressure to the optical measurement device, the resulting signal-to-noise ratio of the detected optical measurement signal, such as a photoplethysmography signal, can be increased, and a more accurate measurement can be obtained from the user. An optimum pressure can be determined in real-time by analyzing the detected optical measurement signal and correlating a high signal-to-noise ratio portion of the signal with a corresponding applied pressure. The user is then provided real-time feedback indicating whether the amount of pressure being applied by the user should be increased, decreased or maintained at the same level in order to continually obtain the highest quality signal. The optical measurement device can therefore provide an optimal pressure determination customized for each individual user, thereby obtaining a resulting optimal measurement signal for each user.

Figure 34:
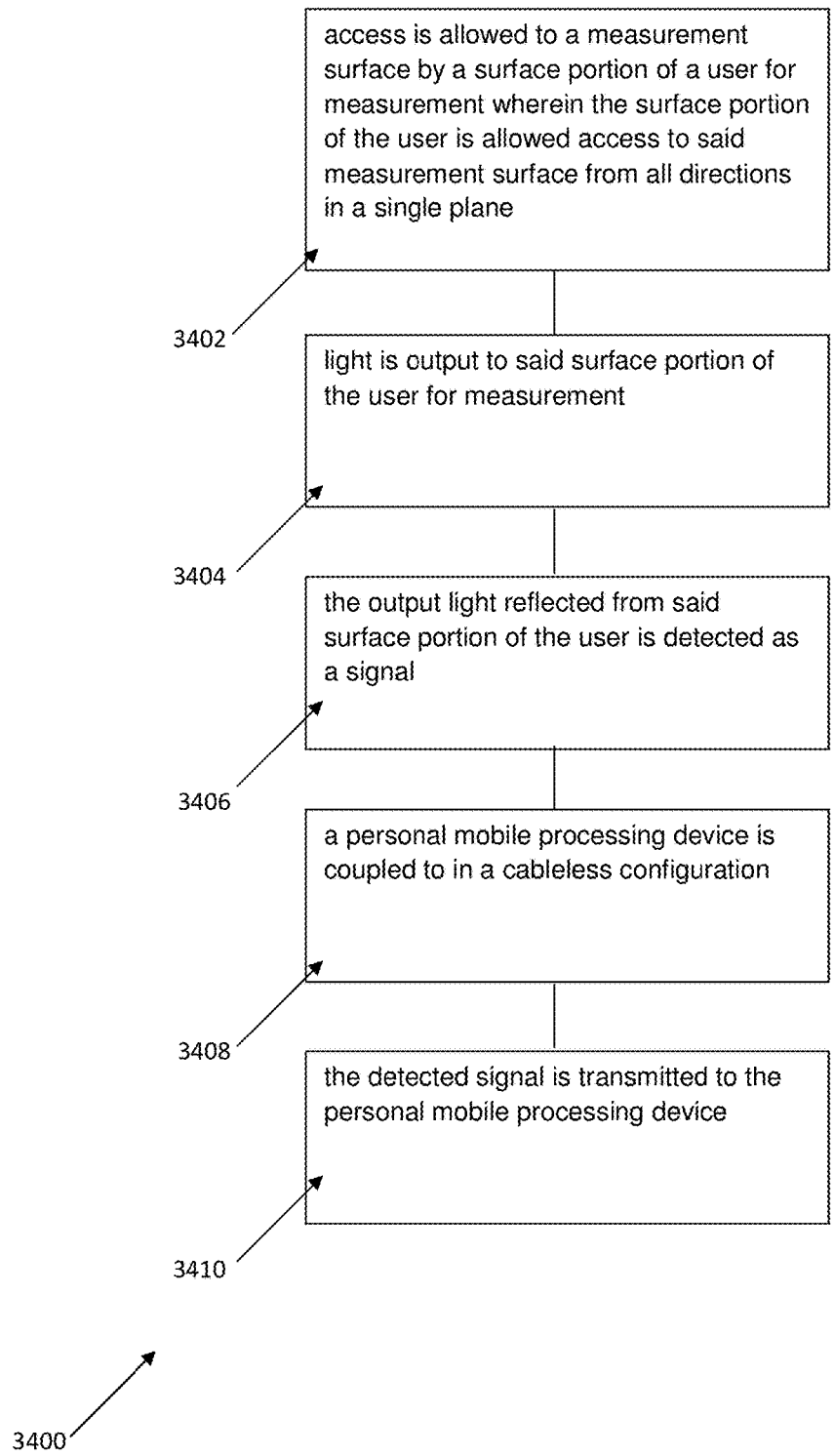
FIG. 34 is a schematic flowchart for illustrating a method for a reflectance-based optical measurement in an example embodiment.

FIG. 34 is a schematic flowchart 3400 for illustrating a method for a reflectance-based optical measurement in an example embodiment. At step 3402, access is allowed to a measurement surface by a surface portion of a user for measurement wherein the surface portion of the user is allowed access to said measurement surface from all directions in a single plane. At step 3404, light is output to said surface portion of the user for measurement. At step 3406, the output light reflected from said surface portion of the user is detected as a signal. At step 3408, a personal mobile processing device is coupled to in a cableless configuration. At step 3410, the detected signal is transmitted to the personal mobile processing device.

Figure 26:
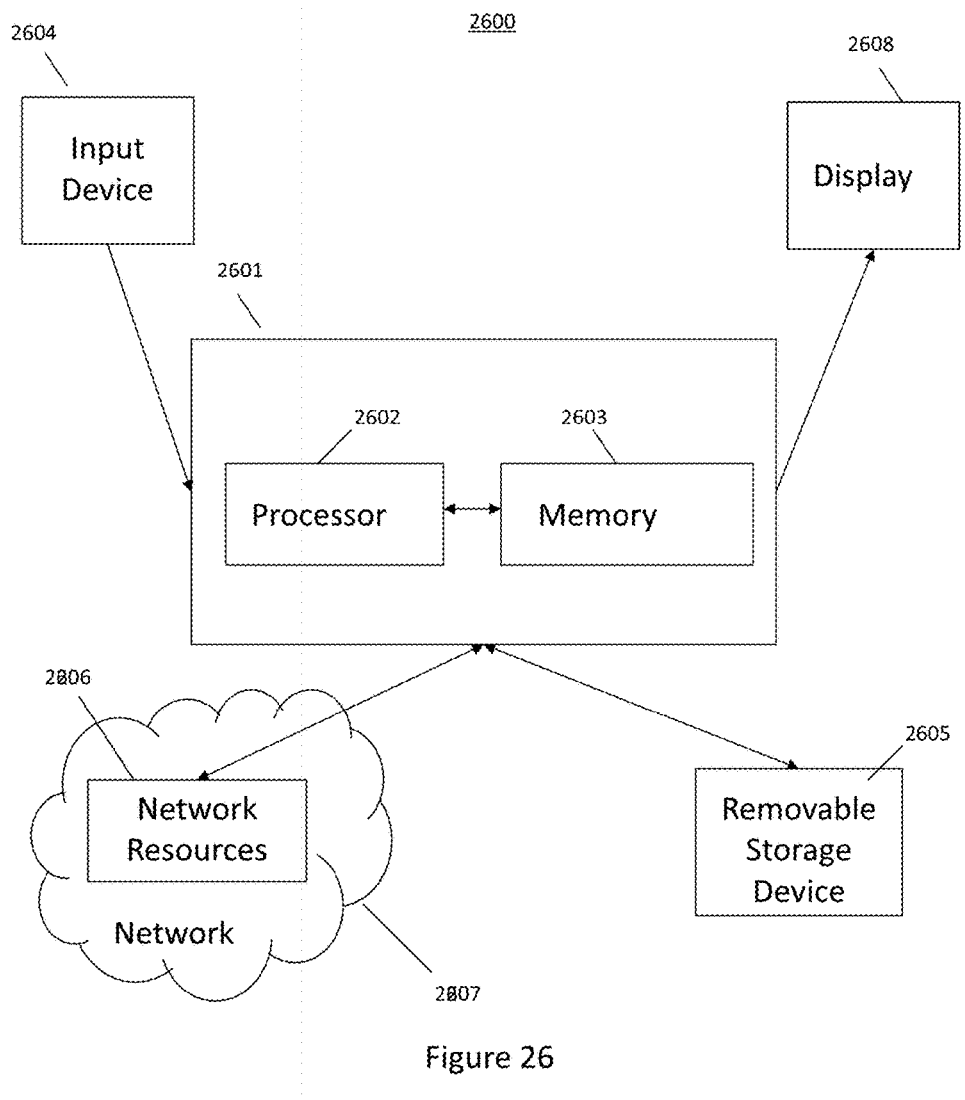
FIG. 26 is a block diagram schematically illustrating an embodiment of a computer/server system suitable for implementing an example embodiment.

FIG. 26 is a block diagram that illustrates an embodiment of a computer/server system 2600 upon which an embodiment of the inventive methodology may be implemented. The system 2600 includes a computer/server platform 2601 including a processor 2602 and memory 2603 which operate to execute instructions, as known to one of skill in the art. The term "computer-readable medium" as used herein refers to any medium that participates in providing instructions to processor 2602 for execution. Additionally, the computer platform 2601 receives input from a plurality of input devices 2604, such as a keyboard, mouse, touch device or verbal command. The computer platform 2601 may additionally be connected to a removable storage device 2605, such as a portable hard drive, optical media (CD or DVD), disk media or any other medium from which a computer can read executable code. The computer platform may further be connected to network resources 2606 which connect to the Internet or other components of a local public or private network. The network resources 2606 may provide instructions and data to the computer platform from a remote location on a network 2607. The connections to the network resources 2606 may be via wireless protocols, such as the 802.11 standards, Bluetooth® or cellular protocols, or via physical transmission media, such as cables or fiber optics. The network resources may include storage devices for storing data and executable instructions at a location separate from the computer platform 2601. The computer interacts with a display 2608 to output data and other information to a user, as well as to request additional instructions and input from the user. The display 2608 may therefore further act as an input device 2604 for interacting with a user.

It will be appreciated by a person skilled in the art that other variations and/or modifications may be made to the specific embodiments without departing from the spirit or scope of the invention as broadly described. The present embodiments are, therefore, to be considered in all respects to be illustrative and not restrictive.

The invention claimed is:

1. A system comprising a personal mobile processing device and reflectance-based optical measurement (RBOM) accessory for removably coupling to the personal mobile processing device, the RBOM accessory comprising:
    an illumination and detection assembly configured to output light to a surface portion of a user for measurement and to detect the output light reflected from said surface portion of the user as a signal;
    a pressure assembly configured to detect an amount of pressure applied to the illumination and detection assembly by said surface portion of the user;
    a coupling member configured for removably coupling in a cableless configuration to the personal mobile processing device; and
    a measurement surface configured to allow access to said measurement surface by the surface portion of the user,
    wherein the RBOM accessory is smaller than palm size,
    wherein said access is provided by the optical accessory being holderless such that the surface portion of the user is allowed access to said measurement surface from all directions in a single plane,
    wherein said coupling member is arranged to transmit the detected signal to the personal mobile processing device for deriving from the detected signal, saturation of peripheral oxygen ($SPO_2$) information of the user, and
    wherein the RBOM accessory is configured to communicate with the personal mobile processing device that is configured to correlate a quality of the detected signal with the amount of pressure by: computing an area under waveforms of detected signals corresponding to a variety of applied pressure amounts, and determining an optimum pressure to correspond a largest computed area, from the variety of applied pressure amounts.

2. The system of claim 1, wherein said single plane is on a same plane as said measurement surface.

3. The system of claim 1, wherein the RBOM accessory being holderless allows an unshielded configuration whereby ambient light noise is transmitted with said detected signal.

4. The system of claim 1, wherein the RBOM accessory further comprises a housing structure for housing the illumination and detection assembly and wherein the housing structure provides structural rigidity to the RBOM accessory.

5. The system of claim 1, wherein said cableless configuration comprises a coupling means of the coupling member in a form of a universal serial bus (USB) port or a 30-pin port.

6. The system of claim 1, wherein the signal is a photoplethysmography (PPG) signal.

7. The system of claim 1, wherein the illumination and detection assembly comprises a red light emitting diode (LED), an infra-red LED or both.

8. The system of claim 7, wherein saturation of peripheral oxygen (SpO2) information of the user is derivable from the detected signal from both the red LED and the infra-red LED.

9. The system of claim 1, wherein the personal mobile processing device is one selected from the group consisting of a mobile phone, a smartphone, a personal digital assistant (PDA), a mobile music player, a tablet computer, a netbook and a laptop.

10. A method for a reflectance-based optical measurement, the method comprising:
    removably coupling a smaller than palm size reflectance-based optical measurement (RBOM) accessory to a personal mobile processing device in a cableless configuration;
    outputting light to a surface portion of a user for measurement;
    detecting the output light reflected from said surface portion of the user as a signal;
    transmitting the detected signal to the personal mobile processing device for deriving from the detected signal, saturation of peripheral oxygen ($SPO_2$) information of the user; and
    correlating a quality of the detected signal with an amount of pressure applied on the RBOM accessory by: computing an area under waveforms of detected signals corresponding to a variety of applied pressure amounts, and determining an optimum pressure to correspond a largest computed area, from the variety of applied pressure amounts.

11. The method of claim 10, wherein the step of detecting the output light is performed in an unshielded configuration whereby ambient light noise is transmitted in the transmitting step with said detected signal.

12. The method of claim 10, further comprising detecting an amount of pressure applied by said surface portion of the user.

13. The method of claim 10, wherein the step of outputting light comprises using a red light emitting diode (LED), an infra-red LED or both.

14. The method of claim 13, further comprising deriving saturation of peripheral oxygen (SPO2) information of the user from the detected signal from both the red LED and the infra-red LED.

15. A non-transitory computer readable data storage medium having stored thereon computer code means for instructing a processor to execute a method for a reflectance-based optical measurement using a smaller than palm size reflectance-based optical measurement (RBOM) accessory removably coupled to a personal mobile processing device in a cableless configuration, the method comprising:
- outputting light to a surface portion of a user for measurement;
- detecting the output light reflected from said surface portion of the user as a signal;
- transmitting the detected signal to the personal mobile processing device for deriving from the detected signal, saturation of peripheral oxygen ($SPO_2$) information of the user; and
- correlating a quality of the detected signal with an amount of pressure applied on the RBOM accessory by: computing an area under waveforms of detected signals corresponding to a variety of applied pressure amounts, and determining an optimum pressure to correspond a largest computed area, from the variety of applied pressure amounts.

16. The non-transitory computer readable data storage medium of claim 15, wherein the method comprises performing the step of detecting the output light in an unshielded configuration whereby ambient light noise is transmitted in the transmitting step with said detected signal.

17. The non-transitory computer readable data storage medium of claim 15, wherein the method comprises using a red light emitting diode (LED), an infra-red LED or both, in the step of outputting light.

18. The non-transitory computer readable data storage medium of claim 17, wherein the method further comprises deriving saturation of peripheral oxygen (SPO2) information of the user from the detected signal from both the red LED and the infra-red LED.

* * * * *